(12) United States Patent
Shmayahu et al.

(10) Patent No.: US 12,347,100 B2
(45) Date of Patent: Jul. 1, 2025

(54) SYSTEMS AND METHODS FOR GENERATING VIRTUAL IMAGES

(71) Applicant: Mazor Robotics Ltd., Caesarea (IL)

(72) Inventors: Yizhaq Shmayahu, Ramat HaSharon (IL); Diego Merkier, Bat Hefer (IL)

(73) Assignee: Mazor Robotics Ltd., Caesarea (IL)

( * ) Notice: Subject to any disclaimer, the term of this patent is extended or adjusted under 35 U.S.C. 154(b) by 403 days.

(21) Appl. No.: 17/490,895

(22) Filed: Sep. 30, 2021

(65) Prior Publication Data

US 2022/0156928 A1    May 19, 2022

Related U.S. Application Data

(60) Provisional application No. 63/116,003, filed on Nov. 19, 2020.

(51) Int. Cl.
*G06T 7/00* (2017.01)
*A61B 34/30* (2016.01)
*G06T 7/13* (2017.01)

(52) U.S. Cl.
CPC ............ *G06T 7/0012* (2013.01); *A61B 34/30* (2016.02); *G06T 7/13* (2017.01);
(Continued)

(58) Field of Classification Search
CPC ................ G06T 7/0012; G06T 7/13; G06T 2207/10116; G06T 2207/10132;
(Continued)

(56) References Cited

U.S. PATENT DOCUMENTS

| 4,897,788 A | 1/1990 | King |
| 4,922,915 A | 5/1990 | Arnold et al. |

(Continued)

FOREIGN PATENT DOCUMENTS

| WO | WO 2019/148154 | 8/2019 | |
| WO | WO-2019148154 A1 * | 8/2019 | ............. A61B 34/10 |

OTHER PUBLICATIONS

Karlsson et al. "Dedicated Magnetic Resonance Imaging in the Radiotherapy Clinic," International Journal of Radiation Oncology, Biology, Physics, 2009, vol. 74, No. 2, pp. 644-651.

(Continued)

*Primary Examiner* — Syed Haider
(74) *Attorney, Agent, or Firm* — Sheridan Ross P.C.

(57) ABSTRACT

A method of generating a virtual MRI image includes receiving an initial MRI image of a patient in a first position, the initial MRI image depicting at least a portion of an anatomy of the patient; receiving a plurality of images of the patient in a second position, each of the plurality of images depicting at least a plurality of bony elements within the portion of the patient's anatomy; receiving soft tissue information corresponding to at least a plurality of soft tissue elements within the portion of the patient's anatomy; segmenting the initial MRI image to identify a depiction of each of the plurality of bony elements and each of the plurality of soft tissue elements within the initial MRI image; and generating a virtual MRI image based on the MRI image, the plurality of images, and the soft tissue information.

19 Claims, 5 Drawing Sheets

(52) U.S. Cl.
CPC .............. *G06T 2207/10116* (2013.01); *G06T 2207/10132* (2013.01); *G06T 2207/30012* (2013.01)

(58) Field of Classification Search
CPC ............ G06T 2207/30012; G06T 7/30; G06T 2207/10088; A61B 34/30; A61B 2090/374; A61B 2034/2065; A61B 2034/2055

See application file for complete search history.

(56) References Cited

U.S. PATENT DOCUMENTS

| | | | |
|---|---|---|---|
| 4,966,599 A | 10/1990 | Pollock | |
| 4,985,906 A | 1/1991 | Arnold | |
| 5,203,346 A | 4/1993 | Fuhr et al. | |
| 5,304,931 A | 4/1994 | Flamig et al. | |
| 5,377,249 A | 12/1994 | Wiesent et al. | |
| 5,448,687 A | 9/1995 | Hoogerhyde et al. | |
| 5,480,440 A | 1/1996 | Kambin | |
| 5,745,542 A | 4/1998 | Gordon et al. | |
| 6,106,464 A | 8/2000 | Bass et al. | |
| 6,149,592 A | 11/2000 | Yanof et al. | |
| 6,185,444 B1 | 2/2001 | Ackerman et al. | |
| 6,226,548 B1 | 5/2001 | Foley et al. | |
| 6,430,252 B2 | 8/2002 | Reinwand et al. | |
| 6,633,686 B1 | 10/2003 | Bakircioglu et al. | |
| 6,680,610 B1 | 1/2004 | Kyriakos et al. | |
| 6,725,080 B2 | 4/2004 | Melkent et al. | |
| 6,740,883 B1 | 5/2004 | Stodilka et al. | |
| 6,920,347 B2 | 7/2005 | Simon et al. | |
| 6,978,166 B2 | 12/2005 | Foley et al. | |
| 6,990,222 B2 | 1/2006 | Arnold | |
| RE39,133 E | 6/2006 | Clayton et al. | |
| 7,139,601 B2 | 11/2006 | Bucholz et al. | |
| 7,148,887 B2 | 12/2006 | Kaufman et al. | |
| 7,277,599 B2 | 10/2007 | Eian et al. | |
| 7,322,982 B2 | 1/2008 | Vincent-Prestigiacomo | |
| 7,474,776 B2 | 1/2009 | Kaufman et al. | |
| 7,486,811 B2 | 2/2009 | Kaufman et al. | |
| 7,499,578 B2 | 3/2009 | Reeves et al. | |
| 7,542,791 B2 | 6/2009 | Mire et al. | |
| 7,545,979 B2 | 6/2009 | Fidrich et al. | |
| 7,558,611 B2 | 7/2009 | Arnold et al. | |
| 7,567,834 B2 | 7/2009 | Clayton et al. | |
| 7,570,791 B2 | 8/2009 | Frank et al. | |
| 7,611,540 B2 | 11/2009 | Clifford et al. | |
| 7,620,146 B2 | 11/2009 | Mostafavi | |
| 7,660,623 B2 | 2/2010 | Hunter et al. | |
| 7,664,298 B2 | 2/2010 | Lang et al. | |
| 7,742,629 B2 | 6/2010 | Zarkh et al. | |
| 7,763,035 B2 | 7/2010 | Melkent et al. | |
| 7,835,778 B2 | 11/2010 | Foley et al. | |
| 7,840,253 B2 | 11/2010 | Tremblay et al. | |
| 7,860,208 B2 | 12/2010 | Haerer et al. | |
| RE42,226 E | 3/2011 | Foley et al. | |
| 7,914,535 B2 | 3/2011 | Assell et al. | |
| 7,936,909 B2 | 5/2011 | Krauss | |
| 7,955,301 B1 | 6/2011 | McKay | |
| 7,972,337 B2 | 7/2011 | Boyajian et al. | |
| 7,994,784 B2 | 8/2011 | Yanasak et al. | |
| 8,014,575 B2 | 9/2011 | Weiss et al. | |
| 8,068,580 B2 | 11/2011 | Lang et al. | |
| 8,070,752 B2 | 12/2011 | Metzger et al. | |
| 8,098,909 B2 | 1/2012 | Hibbard et al. | |
| 8,121,249 B2 | 2/2012 | Wang et al. | |
| 8,121,380 B2 | 2/2012 | Blanchard et al. | |
| 8,135,111 B2 | 3/2012 | Jaffray et al. | |
| 8,160,345 B2 | 4/2012 | Pavlovskaia et al. | |
| 8,165,658 B2 | 4/2012 | Waynik et al. | |
| 8,185,186 B2 | 5/2012 | Ross et al. | |
| 8,186,880 B1 | 5/2012 | Arnold | |
| 8,231,678 B2 | 7/2012 | Lambrecht | |
| 8,241,293 B2 | 8/2012 | Stone et al. | |
| 8,298,237 B2 | 10/2012 | Schoenefeld et al. | |
| 8,407,067 B2 | 3/2013 | Uthgenannt et al. | |
| 8,437,521 B2 | 5/2013 | Lu et al. | |
| 8,483,351 B2 | 7/2013 | Wang et al. | |
| 8,494,614 B2 | 7/2013 | Markowitz et al. | |
| 8,500,451 B2 | 8/2013 | Bronstein et al. | |
| 8,503,745 B2 | 8/2013 | Simon et al. | |
| 8,517,608 B1 | 8/2013 | Arnold | |
| 8,532,807 B2 | 9/2013 | Metzger | |
| 8,548,565 B2 | 10/2013 | Hunter et al. | |
| 8,635,082 B2 | 1/2014 | Woods et al. | |
| 8,638,998 B2 | 1/2014 | Steines et al. | |
| 8,639,009 B2 | 1/2014 | Lang et al. | |
| 8,649,577 B1 | 2/2014 | Arnold et al. | |
| 8,660,329 B2 | 2/2014 | Skalli et al. | |
| 8,717,430 B2 | 5/2014 | Simon et al. | |
| 8,764,760 B2 | 7/2014 | Metzger et al. | |
| 8,771,281 B2 | 7/2014 | Carignan et al. | |
| 9,060,816 B2 | 6/2015 | Abdou | |
| 9,064,307 B2 | 6/2015 | Ayed et al. | |
| 9,084,618 B2 | 7/2015 | Serbousek et al. | |
| 9,087,224 B2 | 7/2015 | Jaffray et al. | |
| 9,198,678 B2 | 12/2015 | Frey et al. | |
| 9,271,845 B2 | 3/2016 | Hunt et al. | |
| 9,289,140 B2 | 3/2016 | Ross et al. | |
| 9,386,939 B1 | 7/2016 | Minkoff | |
| 9,498,501 B2 | 11/2016 | Mistry et al. | |
| 9,524,547 B2 | 12/2016 | Garumann et al. | |
| 9,561,004 B2 | 2/2017 | Forsberg | |
| 9,622,826 B2 | 4/2017 | Diolaiti et al. | |
| 9,623,233 B2 | 4/2017 | Imran | |
| 9,629,520 B2 | 4/2017 | Diolaiti | |
| 9,636,185 B2 | 5/2017 | Quaid et al. | |
| 9,636,226 B2 | 5/2017 | Hunt | |
| 9,681,796 B2 | 6/2017 | Tesar et al. | |
| 9,700,356 B2 | 7/2017 | Donner et al. | |
| 9,717,539 B2 | 8/2017 | Donner et al. | |
| 9,717,563 B2 | 8/2017 | Tognaccini et al. | |
| 9,724,013 B2 | 8/2017 | Peacock, III et al. | |
| 9,743,966 B2 | 8/2017 | Horan et al. | |
| 9,795,446 B2 | 10/2017 | DiMaio et al. | |
| 9,801,546 B2 | 10/2017 | Donner et al. | |
| 9,808,177 B2 | 11/2017 | Claude et al. | |
| 9,826,942 B2 | 11/2017 | Sebok et al. | |
| 9,833,265 B2 | 12/2017 | Donner et al. | |
| 9,858,688 B2 | 1/2018 | Nett et al. | |
| 9,867,989 B2 | 1/2018 | Blum et al. | |
| 9,918,740 B2 | 3/2018 | Uthgenannt et al. | |
| 9,943,552 B2 | 4/2018 | Kihm et al. | |
| 9,956,044 B2 | 5/2018 | Gomez et al. | |
| 9,999,400 B2 | 6/2018 | Behrooz et al. | |
| 10,039,760 B2 | 8/2018 | Bar-Or et al. | |
| 10,045,711 B2 | 8/2018 | Peacock, III et al. | |
| 10,061,111 B2 | 8/2018 | Hillman | |
| 10,064,591 B2 | 9/2018 | Wang et al. | |
| 10,102,640 B2 | 10/2018 | Derda et al. | |
| 10,105,120 B2 | 10/2018 | Rasoulian et al. | |
| 10,179,900 B2 | 1/2019 | Harmon et al. | |
| 10,194,131 B2 | 1/2019 | Casas | |
| 10,206,695 B2 | 2/2019 | Meridew et al. | |
| 10,223,794 B2 | 3/2019 | Schadewaldt et al. | |
| 10,245,439 B1 | 4/2019 | Schwarz et al. | |
| 10,251,578 B2 | 4/2019 | Peacock, III et al. | |
| 10,271,915 B2 | 4/2019 | Diolaiti et al. | |
| 10,275,884 B2 | 4/2019 | Hu et al. | |
| 10,278,711 B2 | 5/2019 | Meridew et al. | |
| 10,368,956 B2 | 8/2019 | Siewerdsen et al. | |
| 2002/0015476 A1 | 2/2002 | Reinwand et al. | |
| 2002/0038118 A1 | 3/2002 | Shoham | |
| 2002/0107573 A1 | 8/2002 | Steinberg | |
| 2002/0161446 A1 | 10/2002 | Bryan et al. | |
| 2003/0035507 A1 | 2/2003 | Hsu et al. | |
| 2003/0088179 A1 | 5/2003 | Seeley et al. | |
| 2003/0095696 A1 | 5/2003 | Reeves et al. | |
| 2003/0097062 A1 | 5/2003 | Toth et al. | |
| 2003/0113003 A1 | 6/2003 | Cline et al. | |
| 2004/0015071 A1 | 1/2004 | Komura et al. | |
| 2004/0015176 A1 | 1/2004 | Cosman | |
| 2004/0019263 A1 | 1/2004 | Jutras et al. | |
| 2004/0039384 A1 | 2/2004 | Boehm, Jr. et al. | |

(56) References Cited

U.S. PATENT DOCUMENTS

| | | |
|---|---|---|
| 2004/0101085 A1 | 5/2004 | Edic |
| 2004/0167398 A1 | 8/2004 | Flohr et al. |
| 2005/0105693 A1 | 5/2005 | Zhao et al. |
| 2005/0123215 A1 | 6/2005 | Man |
| 2005/0154389 A1 | 7/2005 | Selover et al. |
| 2005/0154465 A1 | 7/2005 | Hodges et al. |
| 2005/0154466 A1 | 7/2005 | Humphreys et al. |
| 2005/0156593 A1 | 7/2005 | Assmann et al. |
| 2005/0171608 A1 | 8/2005 | Peterman et al. |
| 2005/0192575 A1 | 9/2005 | Pacheco |
| 2005/0276455 A1 | 12/2005 | Fidrich et al. |
| 2006/0228009 A1 | 10/2006 | Fidrich et al. |
| 2006/0285737 A1 | 12/2006 | Hamill et al. |
| 2007/0015991 A1 | 1/2007 | Fu et al. |
| 2008/0021502 A1 | 1/2008 | Imielinska et al. |
| 2008/0119719 A1 | 5/2008 | Ascenzi et al. |
| 2008/0144907 A1 | 6/2008 | Shen |
| 2008/0159611 A1 | 7/2008 | Tao et al. |
| 2010/0106010 A1 | 4/2010 | Rubner et al. |
| 2011/0021914 A1 | 1/2011 | Zheng et al. |
| 2011/0064291 A1 | 3/2011 | Kelm et al. |
| 2011/0135173 A1 | 6/2011 | Elbaroudi et al. |
| 2011/0158494 A1 | 6/2011 | Bar-Shalev et al. |
| 2011/0172516 A1* | 7/2011 | Sugiura .................. A61B 5/055 345/643 |
| 2011/0269100 A1 | 11/2011 | Furrer et al. |
| 2011/0317898 A1 | 12/2011 | Shi et al. |
| 2011/0319941 A1 | 12/2011 | Bar et al. |
| 2012/0065497 A1 | 3/2012 | Brown et al. |
| 2012/0078310 A1 | 3/2012 | Bernstein |
| 2012/0143037 A1 | 6/2012 | Najarian et al. |
| 2012/0143090 A1 | 6/2012 | Hay et al. |
| 2012/0172858 A1 | 7/2012 | Harrison et al. |
| 2012/0209273 A1 | 8/2012 | Zaretzka et al. |
| 2012/0221007 A1 | 8/2012 | Batten et al. |
| 2013/0053966 A1 | 2/2013 | Jimenez et al. |
| 2013/0077840 A1 | 3/2013 | Blumfield et al. |
| 2013/0218163 A1 | 8/2013 | Frey |
| 2013/0230224 A1 | 9/2013 | Claude et al. |
| 2013/0325360 A1 | 12/2013 | Deciu et al. |
| 2014/0064583 A1 | 3/2014 | Wang et al. |
| 2014/0067069 A1 | 3/2014 | Lopez |
| 2014/0081659 A1 | 3/2014 | Nawana et al. |
| 2014/0177784 A1 | 6/2014 | Yu et al. |
| 2014/0194887 A1 | 7/2014 | Shenoy |
| 2014/0267255 A1 | 9/2014 | Graumann et al. |
| 2014/0277481 A1 | 9/2014 | Lee et al. |
| 2014/0323845 A1 | 10/2014 | Forsberg |
| 2014/0336652 A1 | 11/2014 | Christensen et al. |
| 2014/0378999 A1 | 12/2014 | Crawford et al. |
| 2015/0023988 A1 | 1/2015 | Murray et al. |
| 2015/0080952 A1 | 3/2015 | Drnek et al. |
| 2015/0100127 A1 | 4/2015 | Bal et al. |
| 2015/0196618 A1 | 7/2015 | Burkin et al. |
| 2015/0297246 A1 | 10/2015 | Patel et al. |
| 2016/0007852 A1 | 1/2016 | Warner et al. |
| 2016/0024159 A1 | 1/2016 | Murray et al. |
| 2016/0117817 A1 | 4/2016 | Seel |
| 2016/0135776 A1 | 5/2016 | Chandler, Jr. |
| 2016/0155236 A1* | 6/2016 | Davey .................. G06T 15/08 382/131 |
| 2016/0163050 A1 | 6/2016 | Wang et al. |
| 2016/0180529 A1 | 6/2016 | Rai et al. |
| 2016/0183913 A1 | 6/2016 | Singh et al. |
| 2016/0208248 A1 | 7/2016 | Wirth et al. |
| 2016/0217576 A1* | 7/2016 | Kabus .................. A61B 6/469 |
| 2016/0270931 A1 | 9/2016 | Trieu |
| 2017/0109903 A1 | 4/2017 | Kulon |
| 2017/0196508 A1 | 7/2017 | Hunter |
| 2017/0227430 A1 | 8/2017 | Marini et al. |
| 2017/0245947 A1 | 8/2017 | Bozung et al. |
| 2017/0258526 A1 | 9/2017 | Lang |
| 2017/0325897 A1 | 11/2017 | Isaacs et al. |
| 2017/0325898 A1 | 11/2017 | Isaacs et al. |
| 2018/0056091 A1* | 3/2018 | Jordan .................. A61N 5/107 |
| 2018/0064461 A1 | 3/2018 | Tran et al. |
| 2018/0099009 A1 | 4/2018 | Binette et al. |
| 2018/0110506 A1 | 4/2018 | Thommen et al. |
| 2018/0140245 A1 | 5/2018 | Videman |
| 2018/0168539 A1 | 6/2018 | Singh et al. |
| 2018/0267014 A1 | 9/2018 | Perlson et al. |
| 2018/0303552 A1 | 10/2018 | Ryan et al. |
| 2018/0310993 A1 | 11/2018 | Hobeika et al. |
| 2018/0318014 A1 | 11/2018 | Gangwar et al. |
| 2019/0000372 A1 | 1/2019 | Gullotti et al. |
| 2019/0005687 A1 | 1/2019 | Weingarten et al. |
| 2019/0012783 A1 | 1/2019 | Zahid et al. |
| 2019/0021677 A1 | 1/2019 | Grbic et al. |
| 2019/0029757 A1 | 1/2019 | Roh et al. |
| 2019/0038345 A1 | 2/2019 | Pellegrino et al. |
| 2019/0088360 A1 | 3/2019 | Goble et al. |
| 2019/0105183 A1 | 4/2019 | Adamo et al. |
| 2019/0209080 A1 | 7/2019 | Gullotti et al. |
| 2019/0214126 A1* | 7/2019 | Goetz .................. A61B 6/032 |
| 2019/0216454 A1 | 7/2019 | Thommen et al. |
| 2019/0236389 A1 | 8/2019 | Obaidi |
| 2019/0239868 A1 | 8/2019 | Attenborough |
| 2019/0290361 A1 | 9/2019 | Shalayev et al. |
| 2019/0307393 A1 | 10/2019 | Lotz et al. |
| 2019/0350600 A1 | 11/2019 | Lehman, Jr. et al. |
| 2019/0392552 A1 | 12/2019 | Wang et al. |
| 2021/0192759 A1* | 6/2021 | Lang .................. A61B 90/98 |
| 2021/0279877 A1* | 9/2021 | Conklin .................. A61B 34/10 |
| 2022/0125526 A1* | 4/2022 | Wald .................. A61B 34/10 |

OTHER PUBLICATIONS

Oliviera et al. "Image registration methods for patient-specific virtual physiological human models," Eurographics Workshop on Visual Computing for Biology and Medicine, 2015, pp. 31-40.

Yaniv et al. "Applications of Augmented Reality in the Operating Room," Fundamentals of Wearable Computers and Augmented Reality, Second Edition, Aug. 2015, pp. 485-518.

International Search Report and Written Opinion for International (PCT) Patent Application No. PCT/IL2021/051295, dated Jan. 27, 2022, 15 pages.

Official Action (with English translation) for China Patent Application No. 202180077751.1, dated Apr. 11, 2025, 23 pages.

* cited by examiner

SYSTEMS AND METHODS FOR GENERATING VIRTUAL IMAGES

CROSS REFERENCE TO RELATED APPLICATIONS

This application claims priority to and the benefit of U.S. Provisional Application No. 63/116,003, filed on Nov. 19, 2020, entitled "Systems and Methods for Generating Virtual Images". The entire disclosure of the application listed above is hereby incorporated herein by reference, in its entirety, for all that it teaches and for all purposes.

FIELD

The present technology relates generally to surgical imaging and planning, and more particularly to generating a virtual image of a patient in a desired position.

BACKGROUND

Various imaging modalities are useful for imaging a patient, including, for example, magnetic resonance imaging (MRI), computed tomography (CT), ultrasound, and X-ray imaging. Images of a patient may be taken preoperatively or intraoperatively, and may be used to assist in planning a surgical procedure or updating a plan for a surgical procedure.

SUMMARY

Example aspects of the present disclosure include:

A method of generating a virtual MRI image, comprising: receiving an initial MRI image of a patient in a first position, the initial MRI image depicting at least a portion of an anatomy of the patient; receiving a plurality of images of the patient in a second position, each of the plurality of images depicting at least a plurality of bony elements within the portion of the patient's anatomy; segmenting the initial MRI image to identify a depiction of each of the plurality of bony elements and each of a plurality of soft tissue elements within the initial MRI image; and generating a virtual MRI image based on the MRI image, the plurality of images, and the soft tissue information.

Any of the aspects herein, wherein generating the virtual MRI image comprises: registering each of the plurality of bony elements in the initial MRI image to a corresponding one of the plurality of bony elements depicted in each of the plurality of images.

Any of the aspects herein, wherein generating the virtual MRI image comprises: modifying the depiction of the plurality of soft tissue elements within the initial MRI image based on the soft tissue information.

Any of the aspects herein, further comprising receiving soft tissue information corresponding to at least the plurality of soft tissue elements.

Any of the aspects herein, wherein the soft tissue information comprises a biomechanical model corresponding to the portion of the patient's anatomy, and further wherein the biomechanical model is generated by updating a generic model with dimension information about one or more dimensions of the plurality of soft tissue elements within the portion of the patient's anatomy and composition information about a composition of at least one of the plurality of soft tissue elements within the portion of the patient's anatomy.

Any of the aspects herein, wherein the soft tissue information comprises ultrasound information corresponding to at least some of the portion of the patient's anatomy.

Any of the aspects herein, wherein the plurality of images provides views of the portion of the patient's anatomy that are separated by at least thirty degrees.

Any of the aspects herein, wherein the plurality of images provides orthogonal views of the portion of the patient's anatomy.

Any of the aspects herein, wherein the first position is a supine position and the second position is a standing position.

Any of the aspects herein, wherein the first position is a supine position or a standing position and the second position is a prone position.

Any of the aspects herein, wherein the second position is a position of flexion, a position of extension, or a lateral position.

Any of the aspects herein, wherein the plurality of images comprises at least one X-ray image.

Any of the aspects herein, wherein the plurality of images comprises at least one ultrasound image.

Any of the aspects herein, wherein the plurality of images is obtained intraoperatively.

A system for generating a virtual MRI image, comprising: an imaging device capable of imaging hard tissue; a processor; and a memory storing instructions for execution by the processor. The instructions, when executed, cause the processor to: receive a first MRI image of a patient in a first position, the first MRI image depicting hard tissue and soft tissue of the patient; receiving a plurality of images of the patient in a second position different than the first position, the plurality of images generated by the imaging device; receive soft tissue information corresponding to the patient; process the first MRI image to identify a plurality of bony elements and a plurality of soft tissue elements therein; and generate a virtual second MRI image by registering each of the plurality of bony elements in the first MRI image to a corresponding bony element in the plurality of images, and by updating the plurality of soft tissue elements in the first MRI image based on the soft tissue information.

Any of the aspects herein, wherein the imaging device utilizes X-rays.

Any of the aspects herein, wherein the soft tissue information comprises ultrasound information.

Any of the aspects herein, further comprising: an ultrasound probe; and a robotic arm configured to manipulate at least one of the imaging device and the ultrasound probe.

Any of the aspects herein, wherein the instructions stored in the memory, when executed, further cause the processor to: cause the robotic arm to move the ultrasound probe to a plurality of positions to generate the soft tissue information.

Any of the aspects herein, wherein the first position is a supine position or a standing position.

Any of the aspects herein, wherein the second position is a standing position, a prone position, a lateral position, a position of flexion, or a position of extension.

Any of the aspects herein, wherein each of the plurality of bony elements is a vertebra.

Any of the aspects herein, wherein the plurality of soft tissue elements comprises at least one of a ligament and an intervertebral disc.

Any of the aspects herein, wherein the soft tissue information comprises a biomechanical model.

Any of the aspects herein, wherein the biomechanical model reflects patient-specific dimension and composition information.

A method of modifying image data, comprising: receiving first image data corresponding to a patient's spine in a first position, the first image data comprising first information about a plurality of bony elements of the patient's spine and a plurality of soft tissue elements of the patient's spine; receiving second image data corresponding to at least two images of the patient's spine in a second position different than the first position, the second image data comprising second information about the plurality of bony elements of the patient's spine; receiving soft tissue data corresponding to the plurality of soft tissue elements of the patient's spine; and generating third image data by modifying the first image data based on the second image data and the soft tissue data, the modifying comprising registering the first information to the second information.

Any of the aspects herein, wherein the first image data is generated using magnetic resonance imaging.

Any of the aspects herein, wherein the second image data is generated using an X-ray imaging device.

Any of the aspects herein, wherein the soft tissue data is generated using an ultrasound imaging device.

Any of the aspects herein, wherein the at least two images are offset by at least thirty degrees.

Any of the aspects herein, wherein the at least two images are orthogonal.

Any of the aspects herein, wherein the first image data is in a first format, the second image data is in a second format different than the first format, and the third image data corresponds to a virtual image in the first format of the patient's spine in the second position.

A method of generating virtual image data, comprising: receiving first image data corresponding to a portion of a patient's anatomy in a first pose, the first image data comprising first information about a plurality of bony elements and a plurality of soft tissue elements of the portion of the patient's anatomy; receiving second image data corresponding to the portion of the patient's anatomy in a second pose different than the first pose, the second image data comprising second information about a plurality of bony elements and a plurality of soft tissue elements of the portion of the patient's anatomy; determining, from the first information and the second information, a range of deformation of one or more bony elements of the plurality of bony elements or of one or more soft tissue elements of the plurality of soft tissue elements; updating a biomechanical model based on the determined range of deformation to yield an updated biomechanical model; and generating, based on the first image data, the second image data, and the updated biomechanical model, third image data corresponding to the portion of the patient's anatomy in a third pose different than the first and second poses.

Any of the aspects herein, wherein the first image data and the second image data are generated using magnetic resonance imaging.

Any of the aspects herein, further comprising determining, from the first information and the second information, a range of movement between neighboring anatomical elements in the portion of the patient's anatomy.

Any of the aspects herein, wherein the updating the biomechanical model further comprises updating the biomechanical model based on the determined range of movement.

Any of the aspects herein, wherein the third image data is virtual MRI image data.

Any of the aspects herein, further comprising segmenting one or more anatomical elements in the first image data and the second image data.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
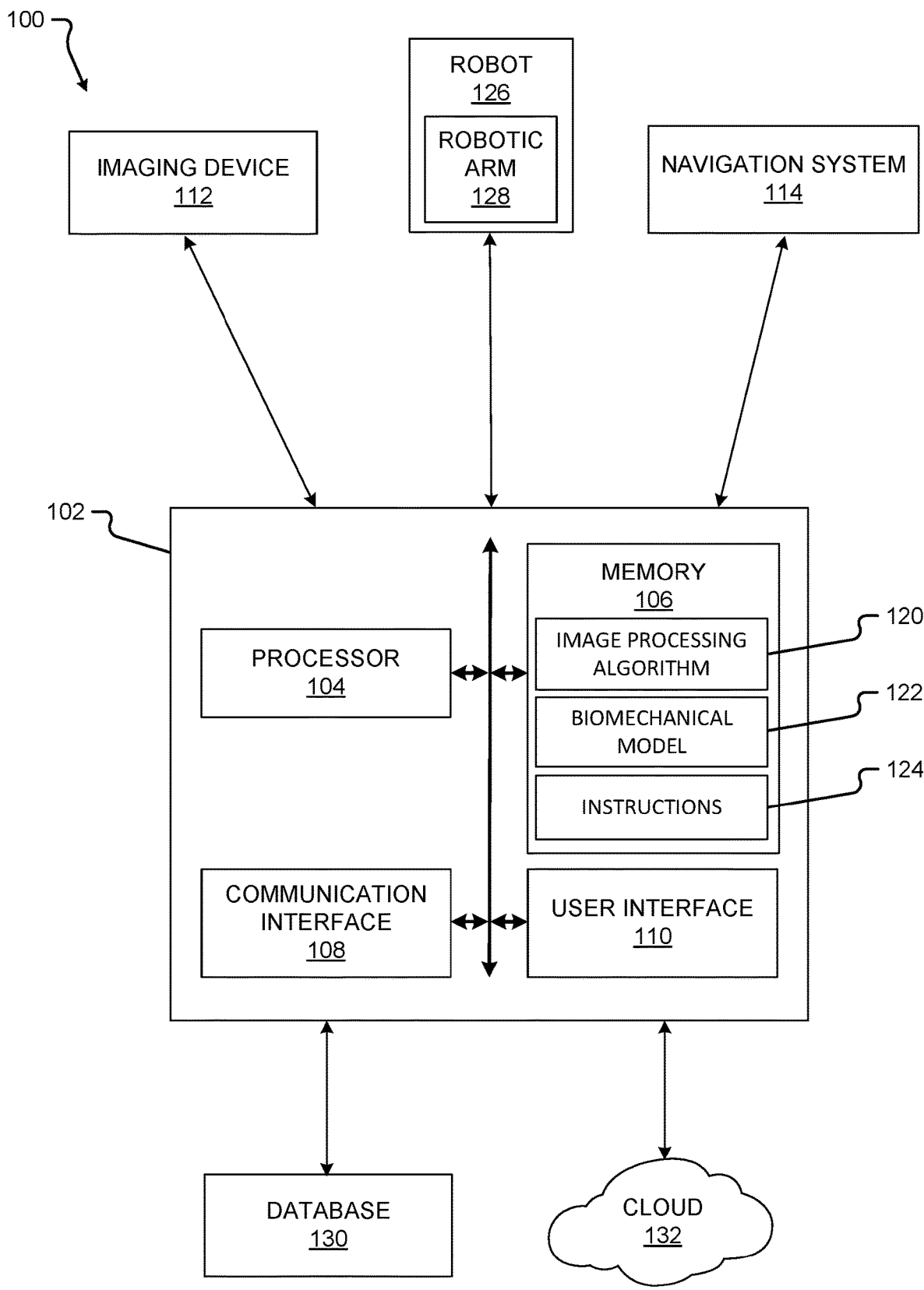
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, A13, or A14 Bionic processors; Apple S series processors; Apple T series processors; Apple W series processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

MRI scans of a patient's spine may be acquired with the patient in a supine position. In this position, the patient may be asymptomatic, and elements compressing the spinal cord or spinal nerves might not be appropriately visualized, as such elements may move into a compression-inducing position only when the patient is standing. The correlation of findings based on supine MRI images with patient symptoms is low. This limits the role of MRI with respect to surgical guidance.

Scanners allowing MRI acquisition in an upright position are beginning to emerge and show better correlation of imaging findings with patient complaints. But these scanners are not widely available.

Standing X-ray images are routinely acquired during the evaluation of spine disease. X-ray images visualize bony structures (e.g., vertebrae) well, but do not visualize well the spinal cord or exiting nerves, or potentially encroaching elements (e.g. intervertebral disc, ligamentum flavum).

The present disclosure describes, for example, the generation of a virtual MRI scan of the spine utilizing: (1) an MRI image of a patient in a first position (e.g., supine, standing); and (2) X-ray images of the patient in a second position (e.g., standing, prone, lateral, position of flexion, position of extension). This may be performed, for example, by co-registering the bony features (e.g., vertebrae) in the MRI image to the X-ray images, and updating soft tissue in the standing bony structure of the resulting image using a biomechanical model or other soft tissue information. The result is a virtual image comprising first image data or information from the MRI image, but of the patient in the second position (e.g., the standing position).

Embodiments of the present disclosure provide information available today only in standing MRI scans (which are rarely available), using widely available images (e.g., standing X-ray images and a supine MRI image).

In other embodiments, the original MRI image is obtained with the patient in a supine position, and a plurality of intra-operative prone X-ray images are used to generate a virtual prone MRI scan in the surgical position. This virtual prone MRI scan may be used to guide robotic or navigated operations, such as decompression or discectomy.

In a third embodiment, the original MRI is taken in a standing position (which is rare today but may become more common in the future) and intra-operative prone X-ray images are used to generate a virtual prone MRI scan in the surgical position. This virtual prone MRI scan may then be used to guide, for example, robotic or navigated operations, such as decompression or discectomy.

Virtual images generated as disclosed herein may demonstrate enhanced correlation with patient signs and symptoms, including in comparison with current standard imaging. Virtual images generated as disclosed herein may also better predict the decompression maneuvers that will be required during surgery to achieve effective and long-lasting decompression. Further, virtual images generated as disclosed herein may be used to modify a preoperative image to reflect a position of a patient during a surgical procedure, thus enabling use of the modified preoperative image in connection with the surgical procedure.

Embodiments of the present disclosure present a technical solution to various technical problems, including, for example, how to obtain an MRI image of a patient in a standing position without an MRI machine capable of scanning a standing patient; how to obtain an intraoperative image of a patient in a prone position without an MRI machine capable of scanning a patient on an operating table; how to obtain an MRI image of a patient in a position of flexion or extension without an MRI machine capable of scanning a patient in such a position, and/or without requiring a patient to remain in such a position for the duration of an MRI scan (which can take as long as thirty minutes or an hour); how to reduce usage (and associated costs) of an MRI machine while still obtaining multiple MRI images of a patient in different positions; and how to obtain an MRI image of a patient in a prone position that can be used to plane a surgical procedure and guide a robot to successfully conduct the surgical procedure without scanning the patient in the prone position.

Turning first to FIG. 1, a block diagram of a system 100 according to at least one embodiment of the present disclosure is shown. The system 100 may be used to process image data; generate a virtual image based on a plurality of images and/or other information; receive an initial MRI image of a patient in a first position; cause an imaging device to obtain images of a patient in a second position; receive a plurality of images of a patient in a second position; cause a robotic arm to move an ultrasound probe to a plurality of positions or poses to generate soft tissue information; identify a plurality of positions or poses for an ultrasound probe or other imaging device in order to assist in the manual navigation of the ultrasound probe or other imaging device to the plurality of positions or poses; receive soft tissue information corresponding to at least a plurality of soft tissue elements of a patient; segment or otherwise process an initial MRI image to identify bony elements and soft tissue elements therein; generate a virtual MRI image; register a plurality of bony elements in an initial MRI image to a plurality of images; modify a depiction of soft-tissue elements in an initial MRI image based on soft tissue information; receive first image data corresponding to a patient's spine in a first position; receive second image data corresponding to images of a patient's spine in a second position; receive soft tissue data; generate third image data by modifying first image data based on second image data and soft tissue data; update a generic, parametric biomechanical model based on patient-specific dimension information, composition information, and/or other information; execute one or more image processing algorithms 120; and/or carry out other aspects of one or more of the methods disclosed herein. The system 100 comprises a computing device 102, one or more imaging devices 112, a navigation system 114, a robot 126, a database 130, and/or a cloud or other network 132. Systems according to other embodiments of the present disclosure may comprise more or fewer components than the system 100. For example, the system 100 may not include the one or more imaging devices 112, the navigation system 114, and/or the robot 126.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions (e.g., the instructions 124) stored in, for example, the memory 106, which instructions may cause the processor 104 to carry out one or more computing steps utilizing or based on data received from the imaging device 112, the robot 126, the navigation system 114, the database 130, and/or the cloud 132.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, 400, 500 and/or 600 described herein. The memory 106 may store, for example, one or more image processing algorithms 120, one or more parametric biomechanical models 122, and/or one or more instructions 124 (e.g., for execution by the processor 104). Such algorithm(s), model(s), and/or instructions may, in some embodiments, be organized into one or more applications, modules, packages, layers, or engines. The algorithm(s), model(s), and/or instructions may cause the processor 104 to manipulate data stored in the memory 106 and/or received from the imaging device 112, the robot 126, the navigation system 114, the database 130, and/or the cloud 132.

The computing device 102 may also comprise a communication interface 108. The communication interface 108 may be used for receiving image data or other information from an external source (such as the imaging device 112, the navigation system 114, the robot 126, the database 130, and/or the cloud 132), and/or for transmitting instructions, images, or other information to an external system or device (e.g., another computing device 102, the navigation system 114, the imaging device 112, the robot 126, the database 130, and/or the cloud 132). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the computing device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding any step or other aspect of any method described herein. In some embodiments, the user interface 110 may be useful to allow a surgeon or other user to create, view, and/or modify a surgical plan; to select one or more image processing algorithms 120 to use in connection with any method disclosed herein; to select a biomechanical model 122 to use in connection with any method disclosed herein; and/or to modify the biomechanical model 122. Any input that may be received from a surgeon or other user via the user interface 110 may alternatively, in some embodiments, be generated automatically by the system 100 (e.g., by the processor 104 or another component of the system 100), or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be capable of taking a 2D image or a 3D image to yield an image and/or image data. "Image data" as used herein refers to the data generated or captured by an imaging device, including in a machine-readable form, a graphical form, and in any other form. In various examples, the image data may comprise data corresponding to an anatomical feature of the patient or a portion thereof (e.g., a spinal region). The imaging device 112 may be or comprise, for example, a CT scanner, a fluoroscope, an O-arm, a C-arm, a G-arm, any other device utilizing X-ray-based imaging, an ultrasound probe, an optical coherence tomography scanner, an endoscope, a telescope, a thermographic camera (e.g., an infrared camera), or any other imaging device suitable for obtaining images or image data corresponding to an anatomical feature of a patient. In some embodiments, the imaging device may be an MRI machine.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, or other objects within the operating room or other room where a surgery takes place. In various embodiments, the navigation system 114 may be used to track a position of the imaging device 112 (or, more particularly, of a navigated reference marker attached, directly or indirectly, in fixed relation to the imaging device 112) and/or of the robot 126 (or, more particularly, of a navigated reference marker attached, directly or indirectly, in fixed relation to the robot 126). The navigation system 114 may include a display for displaying one or more images from an external source (e.g., the computing device 102, an imaging device 112, the database 130, the cloud 132, and/or another source) or a video stream from the camera or other sensor of the navigation system 114.

In some embodiments, the navigation system 114 may be used to track movement of the robot 126 and may provide feedback regarding or confirmation of a position of the robot 126. For example, the navigation system 114 may indicate—audibly and/or visually via a display (e.g., via the user interface 110)—that the robot 126 needs to be moved, automatically or manually, to a suggested robot pose. The navigation system 114 can monitor or track the robot 126 as the robot 126 is moved toward the suggested robot pose. The navigation system 114 can further indicate to or alert a user when the robot 126 has reached the suggested robot pose. In other embodiments, a user may view a display of the navigation system 114 while moving the robot 126 to the suggested robot pose, so as to ensure that the user moves the robot 126 to the correct pose. In some embodiments, the system 100 can operate without the use of the navigation system 114.

The robot 126 may be any surgical robot or surgical robotic system. The robot 126 may be or comprise, for example, the Mazor XTM Stealth Edition robotic guidance system. The robot 126 may comprise one or more robotic arms 128. In some embodiments, the robotic arm 128 may comprise a plurality of robotic arms, though the robot 126 may comprise one robotic arm, two robotic arms, or more than two robotic arms. The robotic arm 128 may be used to selectively hold and/or operate one or more imaging devices 112, and/or any other tool or instrument. In some embodiments, the robotic arm 128 has at least five degrees of freedom. In other embodiments, the robotic arm 128 has at least six degrees of freedom. In yet other embodiments, the robotic arm 128 has fewer than five or greater than six degrees of freedom. The robotic arm 128 (and/or a base of the robot 126) may also have three dimensions of orientation. The combination of multiple degrees of freedom and multiple dimensions of orientation enables the robotic arm 128 to move to any pose. In other words, the robotic arm 128 is not limited to a fixed area and can move in any direction. Further, in some embodiments, the robot 126 can move during a surgical procedure to position the robotic arm 128 (and where the robotic arm 128 is holding an imaging device 112, the imaging device 112) in a desired pose.

The robotic arm 128 may be an accurate robotic arm, such that a pose of the robotic arm (e.g., relative to a robotic coordinate system, or any coordinate system to which the robot 126 is registered) can be precisely determined. The pose of the robotic arm may be determined, for example, based on information from one or more encoders or other sensors that are part of the robot 126 and/or the robotic arm 128.

Reference markers (e.g., navigation markers) may be placed on the robot 126, the robotic arm 128, the imaging device 112, and/or any other object in the surgical space. The reference markers may be tracked by the navigation system 114, and the results of the tracking may be used by the robot 126 and/or by an operator of the system 100 or any component thereof. As described above, in some embodiments, the navigation system 114 can be used to track other components of the system 100 (e.g., the imaging device 112) and the system 100 can operate without the use of the robot 126 (e.g., with the surgeon manually manipulating the imaging device 112).

The database 130 may store one or more images taken by one or more imaging devices 112 and may be configured to provide one or more such images (electronically, in the form of image data) to a computing device such as the computing device 102. The database 130 may be configured to provide image data to a computing device 102 directly (e.g., when the computing device 102 and the database 130 are co-located, and/or are connected to the same local area network) and/or via the cloud 130 (e.g., when the computing device 102 and the database 130 are not co-located or otherwise connected to the same local area network). In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 132 may be or represent the Internet or any other wide area network. The computing device 102 may be connected to the cloud 132 through the communication interface 108, via a wired or wireless connection. In some embodiments, the computing device 102 may communicate with the imaging device 112, the database 130, one or more other computing devices 102, and/or one or more other components of a computing device 102 (e.g., a display or other user interface 110) via the cloud 132.

Figure 2:
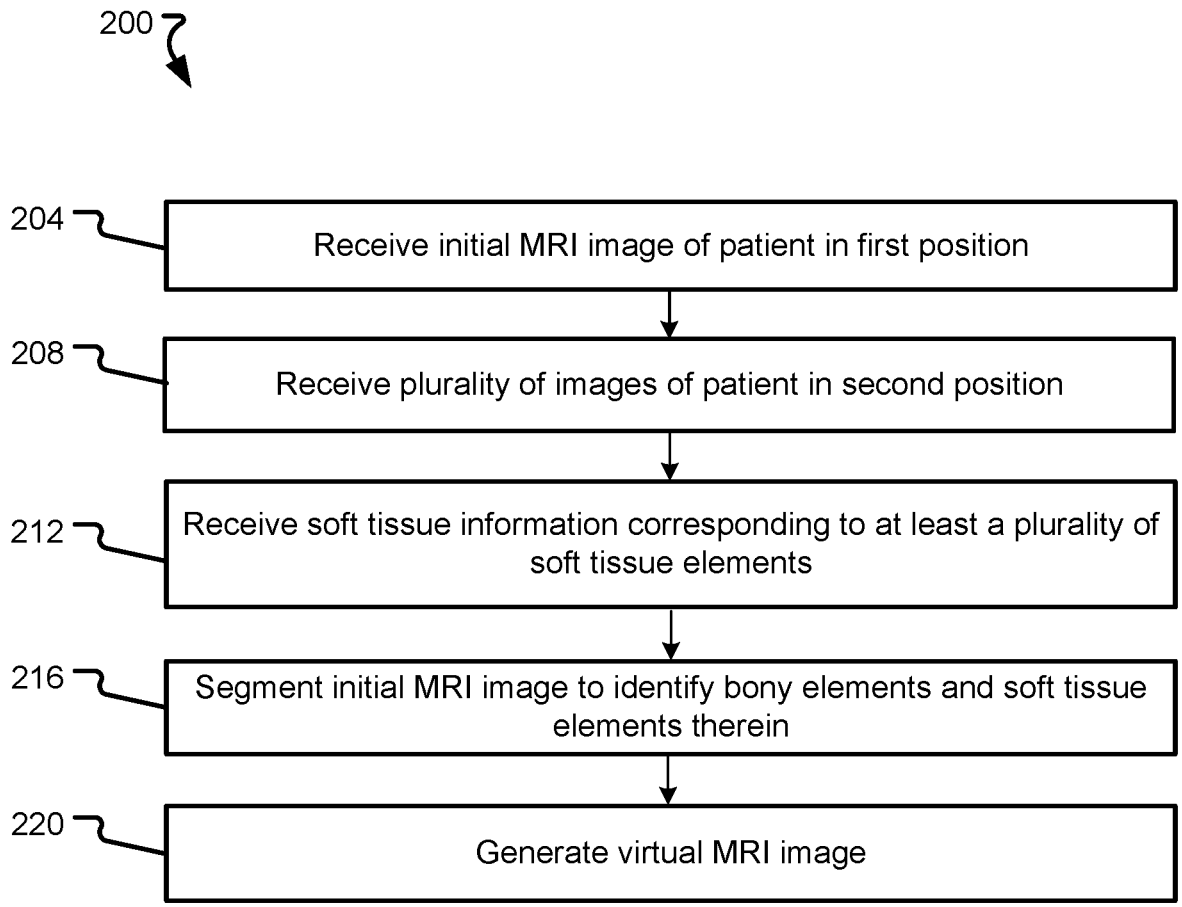
FIG. 2 is a flowchart of a method according to at least one embodiment of the present disclosure.

Turning now to FIG. 2, embodiments of the present disclosure may be used, for example, to generate a virtual MRI image. The virtual MRI image may comprise a comparable level of detail and/or breadth of information as an actual MRI image, but may depict hard and soft tissue of a patient in a position other than a position reflected in the actual MRI image. For example, the present disclosure enables generation of a virtual MRI image showing at least a portion of a patient in a standing position, based on (among other things) an actual MRI image showing the portion of the patient in a supine position. As another example, the present disclosure enables generation of a virtual MRI image showing a portion of a patient in a prone position, based on (again, among other things) an actual MRI image showing the portion of the patient in a supine or a standing position. Embodiments of the present disclosure may be used to generate virtual MRI images showing at least a portion of a patient in a standing position, a prone position, a lateral position, a position of flexion, and a position of extension.

FIG. 2 depicts a method 200 for creating a virtual MRI image. The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 126) or part of a navigation system (such as a navigation system 114). A processor other than any processor described herein may also be used to execute the method 200. The at least one processor may perform the method 200 by executing instructions (such as the instructions 124) stored in a memory such as the memory 106. The instructions may correspond to one or more steps of the method 200 described below. The instructions may cause the processor to execute one or more algorithms, such as an image processing algorithm 120. The instructions may cause the processor to modify one or more aspects of a biomechanical model 122 to reflect patient-specific characteristics or parameters.

The method 200 comprises receiving an initial MRI image of a patient in a first position (step 204). The initial MRI image depicts both hard tissue and soft tissue within at least a portion of an anatomy of the patient. In some embodiments, the initial MRI image may depict a plurality of bony elements and a plurality of soft tissue elements. Thus, for example, the initial MRI image may depict a spine of a patient, or a portion of a spine of a patient, including vertebrae, discs, ligaments, the spinal cord, and/or other anatomical features of or associated with the spine. The initial MRI image may alternatively depict any other portion of a patient's anatomy. In some embodiments, the initial MRI image may depict an entirety of the patient's anatomy. The first position may be a supine position in some embodiments, or a standing position in other embodiments.

The initial MRI image may be received, for example, via a communication interface such as the interface 108. The initial MRI image may be received from a database such as the database 130, a cloud or other network such as the cloud 132, or directly from an MRI imaging device. The initial MRI image may be a preoperative image, and may have been generated, for example, any time in the day, week, or month preceding receipt thereof.

The method 200 also comprises receiving a plurality of images of the patient in a second position (step 208). Each of the plurality of images may depict at least a plurality of bony elements within the portion of the patient's anatomy. Such bony elements are also depicted in the initial MRI image. Thus, for example, where the portion of the patient's anatomy is the patient's spine (or a portion thereof), the images may each depict the vertebrae of the spine (or the portion thereof). Or, where the portion of the patient's anatomy is not the patient's spine, the images may each depict other bony elements within that portion.

In other embodiments, each of the plurality of images may depict at least a plurality of soft tissue elements within the portion of the patient's anatomy. Such soft tissue elements are also depicted in in the initial MRI image. Thus, for example, where the portion of the patient's anatomy is the patient's spine (or a portion thereof), the image may each depict one or more discs, ligaments, and/or other soft tissue elements of the spine. Or, where the portion of the patient's anatomy is not the patient's spine, the images may each depict other soft tissue elements within that portion.

The plurality of images may be or comprise at least one X-ray image, and/or at least one ultrasound image. In some embodiments, the plurality of images may be obtained from a single imaging device, while in other embodiments, the plurality of images may be obtained from a plurality of imaging devices. Also in some embodiments, the plurality of images may be obtained from a plurality of imaging devices having at least two different imaging modalities. In other words, at least one image of the plurality of images may be generating using an imaging device having a first imaging modality, and at least another image of the plurality of images may be generated using an imaging device having a second imaging modality different than the first imaging modality. Imaging devices and modalities that may be used in connection with embodiments of the present disclosure include, for example, O-arms, C-arms, G-arms, fluoroscopes, CT scanners, and/or other devices that utilize X-rays for generating images; ultrasound probes (including single ultrasound transducers and separate ultrasound transmitters and receivers); optical coherence tomography cameras or other optical cameras; and infrared cameras.

Embodiments of the present disclosure in which the plurality of images are or comprise ultrasound images may be particularly advantageous for therapeutic uses of the present disclosure, where a patient is already positioned on an operating table and very precise information about one or more of the patient's bony elements is needed to plan and/or execute a surgical procedure. The ultrasound probe may be, for example, an imaging device 112, and may be manipulated by a robotic arm such as the robotic arm 128. In such embodiments, the robotic arm 128 may move the ultrasound probe to one or more positions that enable the ultrasound probe to obtain desired or needed information about one or more bony elements or soft tissue elements of the patient. In some embodiments, ultrasound probes may generate information about bony or other hard tissue elements, and/or about soft tissue elements, that is more accurate than might be obtained using other imaging modalities, such as X-ray imaging or CT scanning. Information obtained from an ultrasound probe about one or more bony elements may include, for example, information about a position and/or orientation of each bony element (e.g., relative to one or more other hard or soft tissue elements), information about one or more dimensions of each bony tissue element, and/or other information. In some embodiments, information obtained using an ultrasound probe may be used to tailor or fit a biomechanical model (e.g., a biomechanical model 122) comprising hard tissue information and/or soft tissue information to the patient.

In embodiments where an ultrasound probe is used, the ultrasound probe may comprise a single ultrasonic transducer, or an ultrasonic transmitter and a separate ultrasonic receiver. Where an ultrasonic transducer is used, a single robotic arm (such as the robotic arm 128) may be used to position an ultrasonic transducer in one or more poses for obtaining one or more images of the plurality of images, or the ultrasonic transducer may be manually held for such purpose. Where an ultrasonic transmitter and separate ultrasonic receiver are a used, each of the transmitter and the receiver may be held by separate robotic arms. Alternatively, one or both of the transmitter and the receiver may be held manually. In some embodiments, use of a separate ultrasonic transmitter and ultrasonic receiver may beneficially enable more detailed and/or more precise ultrasound images to be obtained than might otherwise be possible with use of a single ultrasonic transducer.

The second position may be a standing position, a prone position, a lateral position (e.g., with the patient resting one side), a position of flexion, or a position of extension. The second position may be a standing position, a position of flexion, or a position of extension when, for example, a healthcare provider wishes to evaluate a source of a patient's symptoms, or for other diagnostic purposes. The second position may be a prone position or a lateral position when, for example, the patient is positioned on an operating table in advance of or during a surgical procedure, and a surgeon or other provider wishes to utilize the additional anatomical detail—soft tissue detail, for example—provided by an MRI image (as opposed to an X-ray image, for example) in connection with the surgical procedure.

The plurality of images provides at least two different views of the portion of the patient's anatomy that are separated by at least thirty degrees. In some embodiments, the two different views provided by the plurality of images may be orthogonal views. In other embodiments, the two different views may be offset from each other by more than thirty degrees and less than ninety degrees.

The plurality of images may be received, for example, via a communication interface such as the interface 108. The plurality of images may be received from a database such as the database 130, a cloud or other network such as the cloud 132, or directly from an imaging device such as the imaging device 112. In some embodiments, the plurality of images may have been generated, for example, any time in the day, week, or month preceding receipt thereof. In other embodiments, the plurality of images may have been obtained immediately in advance of a surgical procedure or during a surgical procedure.

The method 200 also comprises receiving soft issue information corresponding to at least a plurality of soft tissue elements (step 212). The soft tissue elements are also depicted in the initial MRI image. Thus, for example, where the initial MRI image depicts a spine of a patient, the soft tissue information corresponds to soft tissue elements of the patient's spine, such as discs, ligaments, the spinal cord, and/or other soft tissue anatomical features of or associated with the spine. Where the initial MRI image depicts a portion of the patient's anatomy other than the spine, the soft tissue information corresponds to soft tissue elements within that portion of the patient's anatomy.

The soft tissue information may be or include a biomechanical model such as the biomechanical model 122. The biomechanical model corresponds to the portion of the patient's anatomy depicted in the initial MRI image and the plurality of images. In some embodiments, only a portion of a biomechanical model may be used. In other embodiments, multiple biomechanical models—each corresponding to a particular soft tissue element of the anatomy—may be used. For example, in some embodiments, where the portion of the patient's anatomy depicted in the initial MRI image is the patient's spine, only a spine portion of the biomechanical model may be utilized, even though the biomechanical model may comprise additional portions, and may even be a model of an entire human body. In other embodiments, one biomechanical model may be used to represent one or more intervertebral discs depicted in the initial MRI image, another biomechanical model may be used to represent one or more ligaments depicted in the initial MRI image, and so forth.

The biomechanical model may model only the soft tissue of the human body, or the biomechanical model may model both hard and soft tissue of the human body. The model may be a parametric biomechanical model, adjustable based on patient-specific information. For example, the dimensions and composition of a patient's ligaments, intervertebral discs, and other soft tissue elements may be measured, and the resulting measurements may be input to the biomechanical model, or otherwise used to render the otherwise generic biomechanical model specific to the patient. Other parameters may also be used to more closely match the biomechanical model to the patient, such as information about the patient's age and/or range of motion.

In some embodiments, the soft tissue information may be or comprise information obtained using an ultrasound probe. Such embodiments may be particularly advantageous for therapeutic uses of the present disclosure, where a patient is already positioned on an operating table and very precise information about one or more of the patient's soft tissue elements is needed to plan and/or execute a surgical procedure. The ultrasound probe may be, for example, an imaging device 112, and may be manipulated by a robotic arm such as the robotic arm 128. In such embodiments, the robotic arm 128 may move the ultrasound probe to one or more positions that enable the ultrasound probe to obtain desired or needed information about one or more soft tissue elements of the patient. In some embodiments, ultrasound probes may generate information about soft tissue elements that is more accurate than information in a biomechanical model. For example, use of soft tissue information from a biomechanical model for purposes of the present disclosure may result in 1-2 mm of error, while use of soft tissue information from an ultrasound probe for purposes of the present disclosure may result in less than 1 mm of error. Soft tissue information obtained from an ultrasound probe may include, for example, information about a position and/or orientation of each soft tissue element (e.g., relative to one or more other hard or soft tissue elements), information about one or more dimensions of each soft tissue element, and/or other information. In some embodiments, information obtained using an ultrasound probe may be used to tailor or fit a biomechanical model to the patient.

Also in some embodiments, the soft tissue information may be obtained from an imaging device other than an ultrasound imaging device. Imaging devices and modalities that may be used to obtain soft tissue information in connection with embodiments of the present disclosure include, for example, CT scanners; ultrasound probes (including single ultrasound transducers and separate ultrasound transmitters and receivers); optical coherence tomography cameras or other optical cameras; and infrared cameras.

In some embodiments of the method 200, the step 212 instead comprises receiving hard issue information corresponding to at least a plurality of hard tissue elements (step 212). The hard tissue elements are depicted in the initial MRI image. Thus, for example, where the initial MRI image depicts a spine of a patient, the hard tissue information corresponds to hard tissue elements of the patient's spine, such as vertebrae. Where the initial MRI image depicts a portion of the patient's anatomy other than the spine, the hard tissue information corresponds to hard tissue elements within that portion of the patient's anatomy.

In such embodiments, the hard tissue information may be or include a biomechanical model such as the biomechanical model 122. The biomechanical model corresponds to the portion of the patient's anatomy depicted in the initial MRI image and the plurality of images. In some embodiments, only a portion of a biomechanical model may be used. In other embodiments, multiple biomechanical models—each corresponding to a particular hard tissue element of the anatomy—may be used. For example, in some embodiments, where the portion of the patient's anatomy depicted in the initial MRI image is the patient's spine, only a spine portion of the biomechanical model may be utilized, even though the biomechanical model may comprise additional portions, and may even be a model of an entire human body. In other embodiments, one biomechanical model may be used to represent one or more vertebrae depicted in the initial MRI image, another biomechanical model may be used to represent other vertebrae depicted in the initial MRI image, and so forth.

The biomechanical model may model only the hard tissue of the human body, or the biomechanical model may model both hard and soft tissue of the human body. The model may be a parametric biomechanical model, adjustable based on patient-specific information. For example, the dimensions and/or composition of a patient's vertebrae may be measured, and the resulting measurements may be input to the biomechanical model, or otherwise used to render the otherwise generic biomechanical model specific to the patient. Other parameters may also be used to more closely match the biomechanical model to the patient, such as information about the patient's age and/or range of motion.

In some embodiments, the hard tissue information may be or comprise information obtained using an X-ray imager, ultrasound probe, or other imaging device. Such embodiments may be particularly advantageous for therapeutic uses of the present disclosure, where a patient is already positioned on an operating table and very precise information about one or more of the patient's hard tissue elements is needed to plan and/or execute a surgical procedure. The imaging device may be, for example, an imaging device 112, and may be manipulated by a robotic arm such as the robotic arm 128. In such embodiments, the robotic arm 128 may move the imaging device to one or more positions that enable the imaging device to obtain desired or needed information about one or more hard tissue elements of the patient. In some embodiments, the imaging device may generate information about hard tissue elements that is more accurate than information in a biomechanical model. For example, use of hard tissue information from a biomechanical model for purposes of the present disclosure may result in 1-2 mm of error, while use of hard tissue information from an imaging device for purposes of the present disclosure may result in less than 1 mm of error. Hard tissue information obtained from an imaging device may include, for example, information about a position and/or orientation of each hard tissue element (e.g., relative to one or more other hard or soft tissue elements), information about one or more dimensions of each hard tissue element, and/or other information. In some embodiments, information obtained using an imaging device may be used to tailor or fit a biomechanical model to the patient.

The method 200 also comprises segmenting the initial MRI image to identify a depiction of each of the plurality of bony elements and each of the plurality of soft tissue elements within the MRI image (step 216). The segmentation may be accomplished using one or more image processing algorithms, such as the image processing algorithm 120. The image processing algorithm may be or comprise an algorithm generated using machine learning or other artificial intelligence and may be configured to detect anatomical elements in an image based on training data comprising labeled images of anatomical elements. The image processing algorithm may be or comprise an edge detection algorithm configured to detect the edges of an anatomical element. The image processing algorithm may be a feature recognition algorithm configured to detect one or more anatomical features in an image. Any other image processing algorithm, and/or any combination of image processing algorithms, may be used to segment the plurality of bony elements and the plurality of soft tissue elements.

The segmentation of the plurality of bony elements and the plurality of soft tissue elements in the initial MRI image enables each of the plurality of bony elements and each of the plurality of soft tissue elements within the initial MRI image to be individually moved or otherwise modified, without necessarily changing the rest of the image to the same degree or at all (e.g., to reflect situations where some anatomical portions have moved in different amounts than other anatomical portions or not at all). Thus, for example, once the initial MRI image has been segmented, the boundaries of each vertebra or other bony element depicted in the image is known, such that the depiction of any particular bony element in the image may be moved to a new position and orientation (e.g., a new pose) without necessarily requiring the same movement of the remainder of the anatomical portions in the initial MRI image.

The method 200 also comprises generating a virtual MRI image (step 220). The virtual MRI image is generated using the initial MRI image, the plurality of images, and the soft (or hard) tissue information. More details about registering the virtual MRI image are provided below in connection with FIG. 3 and the corresponding method 300. The virtual MRI image depicts the portion of the patient's anatomy in the second position, even though the initial MRI image only showed the portion of the patient's anatomy in the first position. As a result, where an MRI image of a patient in a particular position cannot be obtained directly—whether because MRI imaging devices are incapable of obtaining images of the patient in the particular position, or because the patient is not capable of maintaining the particular position for the duration of an MRI scan, or because an MRI imaging device that is capable of obtaining images of the patient in the particular position is unavailable or overly expensive to use, or because the initial MRI image has already been taken (e.g., before a different desired pose could be specified), or because the initial MRI image needs to be of the patient (or a portion thereof) in a position other than the desired position for diagnostic or other reasons—the present disclosure may be used to generate a virtual MRI image that shows the various bony and soft tissue elements of imaged portion of the patient in a different position than the position in which those elements were imaged in the initial MRI image. These embodiments of the present disclosure therefore beneficially enables reduced costs, the provision of improved information to healthcare providers (including information that otherwise would be unavailable or difficult to obtain), and reduced use of expensive resources (such as MRI imaging devices).

The present disclosure encompasses embodiments of the method 200 that comprise more or fewer steps than those described above, and/or one or more steps that are different than the steps described above.

Figure 3:
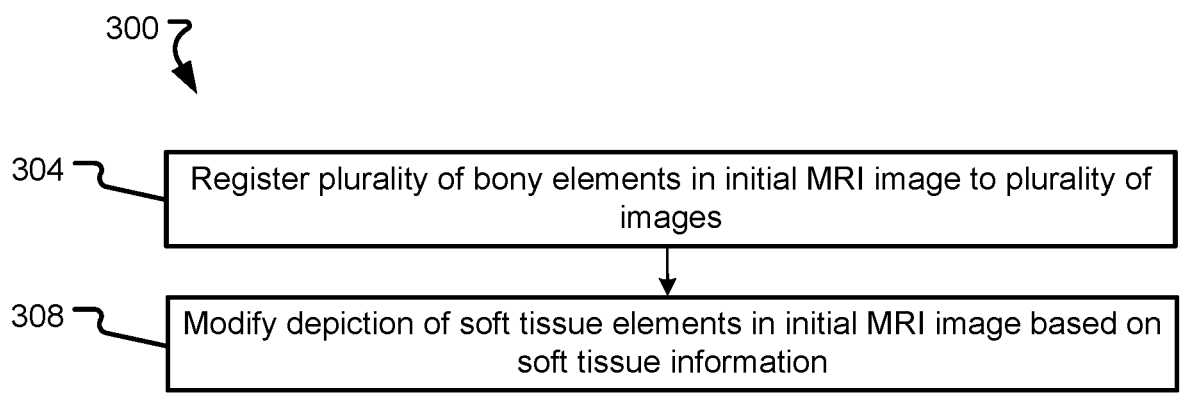
FIG. 3 is a flowchart of a method according to at least one embodiment of the present disclosure.

FIG. 3 depicts a method 300 of generating a virtual MRI image or otherwise generating image data. The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 126) or part of a navigation system (such as a navigation system 114). A processor other than any processor described herein may also be used to execute the method 300. The at least one processor may perform the method 300 by executing instructions (such as the instructions 124) stored in a memory (such as the memory 106). The instructions may correspond to one or more steps of the method 300 described below. The instructions may cause the processor to execute one or more algorithms, such as an image processing algorithm 120. The instructions may cause the processor to modify one or more aspects of a biomechanical model 122 to reflect patient-specific characteristics or parameters.

The steps of the method 300 may correspond to the step 220 of the method 200, the step 424 of the method 400 (described below), step 516 of the method 500 (also described below), and/or step 628 of the method 600 (also described below). In other words, the step 220 of the method 200, the step 424 of the method 400, the step 516 of the method 500, and/or the step 628 of the method 600 may comprise completing one or more steps of the method 300.

The method 300 comprises registering a plurality of bony elements in an initial MRI image to each of a plurality of images (step 304). The initial MRI image may be the same as the initial MRI image described above in connection with the step 204 of the method 200, and the plurality of images may be the same as the plurality of images described above in connection with the step 208 of the method 200. Both the initial MRI image and the plurality of images depict a plurality of bony elements of a portion of a patient's anatomy. Thus, for example, where the portion of the patient's anatomy is the patient's spine, the initial MRI image and each of the plurality of images may depict a plurality of vertebra. Each of the plurality of bony elements is depicted in the initial MRI image and in each of the plurality of images.

The initial MRI image depicts the portion of the patient's anatomy when the patient is in a first position, and the plurality of images depicts the portion of the patient's anatomy when the patient is in a second position different than the first position. The first position may be, for example, a supine or standing position, and the second position may be, for example, a standing position, a prone position, a lateral position (e.g., with the patient on his or her side), a position of flexion, or a position of extension. Moreover, the images in the plurality of images depict the portion of the patient's anatomy from different angles that are offset from each other by at least thirty degrees. This helps to ensure that the three-dimensional pose of each of the plurality of bony elements (with the patient in the second position) can be accurately determined from the plurality of images.

The registering may comprise using one or more algorithms to align each bony element of the plurality of bony elements as depicted in the initial MRI image with the corresponding bony element of the plurality of bony elements as depicted in the plurality of images. For example, if a particular vertebra is depicted in one pose (position and orientation) in the initial MRI image, and in a different pose in the plurality of images, then the registering comprises changing the pose of the particular vertebra as depicted in the initial MRI image to match the pose of that particular vertebra in the plurality of images. This re-alignment or registration is repeated for each of the plurality of bony elements.

The method 300 also comprises modifying a depiction of soft tissue elements in an initial MRI image based on soft tissue information (step 308). The soft tissue information may be the same as the soft tissue information described above in connection with the step 212 of the method 200. The soft tissue information may comprise a biomechanical model of a portion of the patient depicted in the initial MRI image and in the plurality of images, and/or ultrasound information about some or all of the portion of the patient depicted in the initial MRI image and in the plurality of images. In particular, the soft tissue information may comprise information about a plurality of soft tissue elements in the portion of the patient, which information is sufficient to enable a depiction of the plurality of soft tissue elements within the initial MRI image to be updated based on the changes (described above with respect to the step 304) to the poses of the depicted plurality of bony elements.

The modifying may comprise using one or more algorithms and/or completing one or more calculations to determine an updated pose for each one of the plurality of soft tissue elements given the changes to the poses of the depicted plurality of bony elements. Thus, for example, where the pose of each of a plurality of vertebrae has been changed (e.g., during registration of the plurality of bony elements depicted in the initial MRI image to the corresponding plurality of bony elements depicted in the plurality of images), the modifying may comprise determining how the updated pose of two of the plurality of vertebrae would affect the pose of an intervertebral disc in between the two of the plurality of vertebrae, and then adjusting the depiction of the intervertebral disc in the initial MRI image based on the results of that determination. This process may be repeated for each soft tissue element whose pose is affected by the pose of one or more of the plurality of bony elements.

Where the soft tissue information comprises a biomechanical model, the biomechanical model may be used to predict a pose of a soft tissue element given a pose of one or more bony elements to which the soft tissue element is connected. Where the soft tissue information comprises ultrasound data, the ultrasound data may reflect the actual pose of a soft tissue element (with the patient in the second position), such that the depiction of the soft tissue elements in the initial MRI image may be modified even more accurately.

The method 300 yields a virtual MRI image that comprises the level of detail of an MRI image but depicts the originally imaged portion of the patient in a position different than that of the initial MRI image. Such position may be a position that cannot be imaged in an MRI imaging device (whether due to applicable size constraints, inability of a patient to assume the desired position for the duration of an MRI scan, unavailability of the MRI device, or otherwise), and/or a position that enables better diagnostic or therapeutic care with reduced consumption of scarce resources (e.g., by reducing the amount of MRI machine use, including by enabling a single MRI image depicting a portion of a patient in a first position to be used to generate one or more virtual MRI images, each depicting at least the portion of the patient in a different position than the first position). For example, an initial MRI image of a patient's spine with the patient in the supine position may be utilized to create, using embodiments of the present disclosure, virtual MRI images of the patient's spine with the patient in a standing position, a position of flexion, and a position of extension. These virtual MRI images may then be used to better diagnose the source of a patient's back pain or other symptoms; to analyze alternative potential treatments and the effects thereof; and/or to plan one or more surgical procedures with a higher degree of precision and safety than would otherwise be possible due to the higher amount of detail, regarding both bony tissue and soft tissue, in the virtual MRI images.

In some embodiments, one or more virtual MRI images may be used to conduct finite element analysis (e.g., using finite element methods) on one or more anatomical elements of a patient, which may further assist in diagnostic and therapeutic treatment of a patient. The one or more virtual MRI images may be used to measure angles or other dimensions (e.g., for determining the extent of a patient's condition, and/or an extent to which a surgical procedure has been successful, and/or a degree of completion of an in-progress surgical procedure).

Virtual MRI images have the further advantage of being creatable intraoperatively, while a patient is on an operating table. As long as an initial MRI image has been obtained beforehand, imaging devices that are common to operating rooms—including, for example, X-ray imaging devices and/or ultrasound imaging devices—may be used to obtain images of a patient in a prone or other position suitable for the surgical procedure being performed, and such images may be used, together with the initial MRI image, to generate one or more virtual MRI images for consideration and use by the surgeon or other healthcare provider.

Where the method 300 is used in connection with embodiments of the method 200 that incorporate the alternative implementation of the step 212 (e.g., which comprises receiving hard tissue information corresponding to at least a plurality of hard tissue elements), then the step 304 comprises registering a plurality of soft tissue elements in the initial MRI image to the plurality of images, and the step 308 comprises modifying the depiction of hard tissue elements in the initial MRI image based on the hard tissue information.

Where the method 300 is used in connection with the step 424 of the method 400, references to the initial MRI image, the plurality of images, and the virtual MRI image in the foregoing description of the method 300 should be understood as referring to the first MRI image, the plurality of images, and the virtual second MRI image, respectively, each of which is described below. Where the method 300 is used in connection with the step 516 of the method 500, references to the initial MRI image, the plurality of images, and the virtual MRI image in the foregoing description of the method 300 should be understood as referring to the first image data, the second image data, and the third image data, respectively, each of which is described below. Where the method 300 is used in connection with the step 628 of the method 600, references to the initial MRI image, the plurality of images, and the virtual MRI image in the foregoing description of the method 300 should be understood as referring to the first MRI image data, the second MRI image data, and the third MRI image data, respectively, each of which is described below.

The present disclosure encompasses embodiments of the method 300 that comprise more or fewer steps than those described above, and/or one or more steps that are different than the steps described above.

Figure 4:
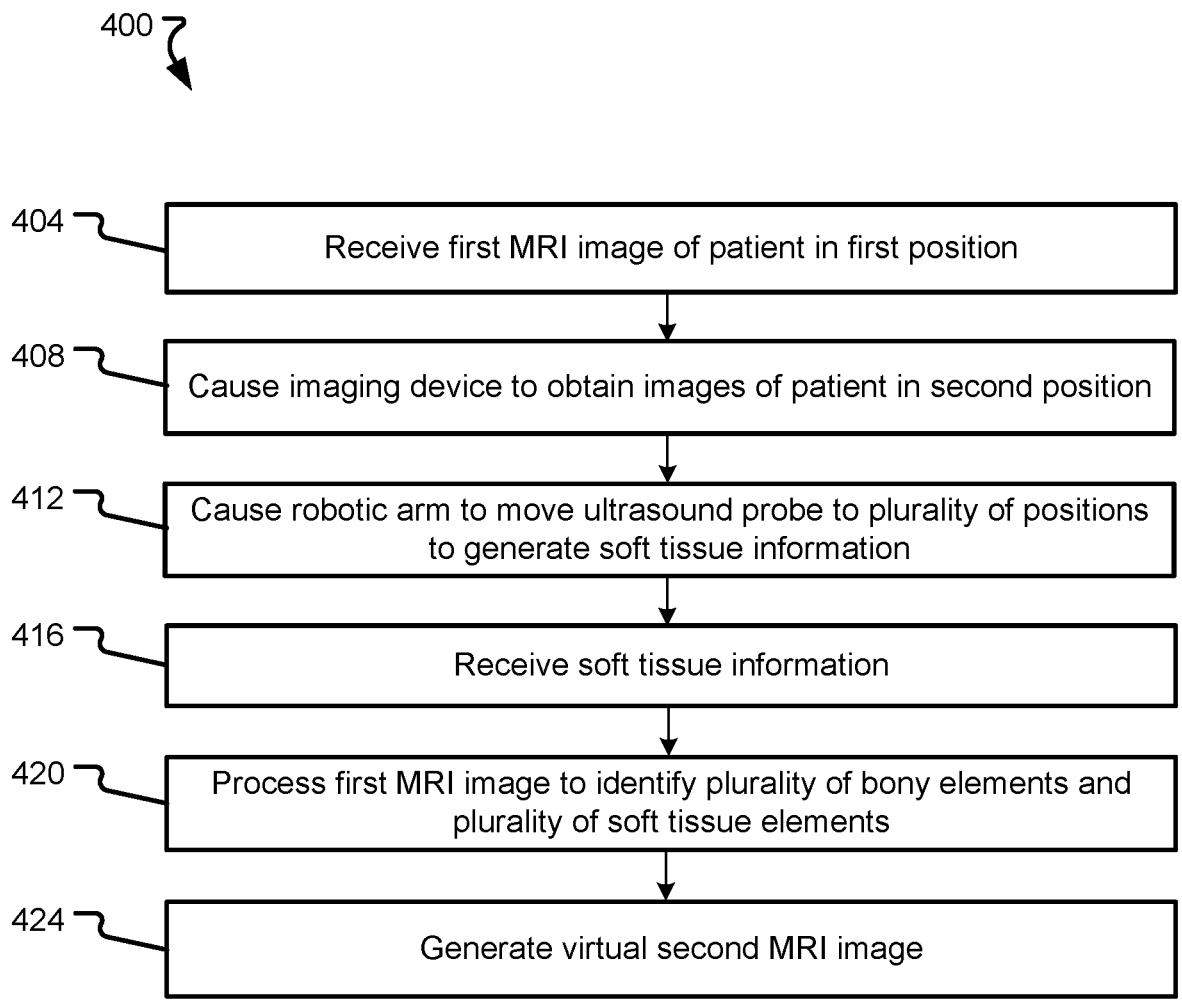
FIG. 4 is a flowchart of a method according to at least one embodiment of the present disclosure.

FIG. 4 depicts a method 400 of generating a virtual MRI image. The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 126) or part of a navigation system (such as a navigation system 114). A processor other than any processor described herein may also be used to execute the method 400. The at least one processor may perform the method 400 by executing instructions (such as the instructions 124) stored in a memory such as the memory 106. The instructions may correspond to one or more steps of the method 400 described below. The instructions may cause the processor to execute one or more algorithms, such as an image processing algorithm 120. The instructions may cause the processor to modify one or more aspects of a biomechanical model 122 to reflect patient-specific characteristics or parameters.

The method 400 comprises receiving a first MRI image of a patient in a first position (step 404). The step 404 may be the same as or substantially similar to the step 204 of the method 200, as described above, and/or vice versa. In particular, the first MRI image may be received from any source and via any component of, for example, a system such as the system 100. The first MRI image depicts both hard tissue and soft tissue of a patient. Additionally, the first MRI image may depict a particular portion of a patient's anatomy, such as the patient's spine, or an entirety of the patient's anatomy. The first position may be, for example, a supine position, a standing position, or another position.

The method 400 also comprises causing an imaging device to obtain a plurality of images of the patient in a second position different than the first position (step 408). One or more aspects of the step 408 may be the same as or substantially similar to one or more aspects of the step 208 of the method 200. The plurality of images depict at least hard tissue in the imaged portion of the patient's anatomy. In some embodiments, the plurality of images depicts substantially the same portion of the patient's anatomy as the first MRI image. In other embodiments, the plurality of images and the first MRI image do not depict substantially the same portion of the patient's anatomy, but there is at least some overlap between the portions of the patient's anatomy depicted by the plurality of images and the first MRI image, respectively, the area of overlap corresponding to an area of interest of the patient.

The imaging device may be the same as or similar to the imaging device 112 described above, and may be configured to generate images using X-rays, ultrasound, or other imaging technology sufficient to image bony anatomical elements and/or other hard tissue. The images in the plurality of images are obtained at different angles that are offset from each other by at least thirty degrees. In some embodiments, the images in the plurality of images are orthogonal to each other.

The imaging device may be positioned manually to obtain the plurality of images, or the imaging device may be automatically positioned to obtain the plurality of images. Similarly, the positions from which the plurality of images are taken may be determined manually (e.g., by a surgeon or other user) or automatically (e.g., without human input as to such positions). In some embodiments, the imaging device may be held by a robotic arm, such as the robotic arm 128, the position of which may be controlled manually or automatically.

The plurality of images comprises at least two images, but may also comprise three images, four images, or more than four images.

The method 400 also comprises receiving soft tissue information corresponding to the patient (step 416). The step 416 may be the same as or substantially similar to the step 212 of the method 200 described above, and/or vice versa. The soft tissue information corresponds to at least some of the soft tissue depicted in the first MRI image. The soft tissue information may be received from an imaging device such as the imaging device 112, which may be, for example, an ultrasound imaging device. In such embodiments, the ultrasound imaging device may be positioned in the same way as the imaging device used to obtain the plurality of images in the step 412, as described above, including manually and/or automatically, whether using a robotic arm such as the robotic arm 128 or not. The ultrasound probe may be moved (whether manually, or using a robotic arm, or otherwise) to multiple positions in order to generate soft tissue information about one or more soft tissue elements. The positions to which the ultrasound probe are moved may be determined by a user of the ultrasound probe or by a processor such as the processor 104 of the computing device 102.

The method 400 also comprises processing the first MRI image to identify a plurality of bony elements and a plurality of soft tissue elements therein (step 420). The step 420 may be the same as or similar to the step 216 of the method 200 described above, and/or vice versa. For example, the processing may comprise utilizing one or more image processing algorithms, such as a feature recognition algorithm, an edge detection algorithm, and/or a segmentation algorithm, to identify the boundaries of each of the plurality of bony elements and each of the plurality of soft tissue elements within the first MRI image.

Similarly to the step 216, the step 420 yields a segmented first MRI image, which segmentation enables each of a plurality of bony elements (e.g. hard tissue elements) and each of the plurality of soft tissue elements within the first MRI image to be individually moved or otherwise modified, without changing the rest of the image. This, in turn, facilitates creation of a virtual MRI image in which the various bony elements in the first MRI image have been moved and/or otherwise modified to match the corresponding bony elements in the plurality of images, and the various soft tissue elements in the first MRI image have been moved and/or otherwise modified to match or otherwise based upon the soft tissue information.

The method 400 also comprises generating a virtual second MRI image (step 424). The virtual second MRI image is generated by registering each of the plurality of bony elements in the first MRI image to a corresponding bony element in the plurality of images, and by updating the plurality of soft tissue elements in the first MRI image based on the soft tissue information. The step 424 may be the same as or substantially similar to the step 220 of the method 200 described above, and/or may comprise one or more steps of the method 300, also described above.

The present disclosure encompasses embodiments of the method 400 that comprise more or fewer steps than those described above, and/or one or more steps that are different than the steps described above.

Figure 5:
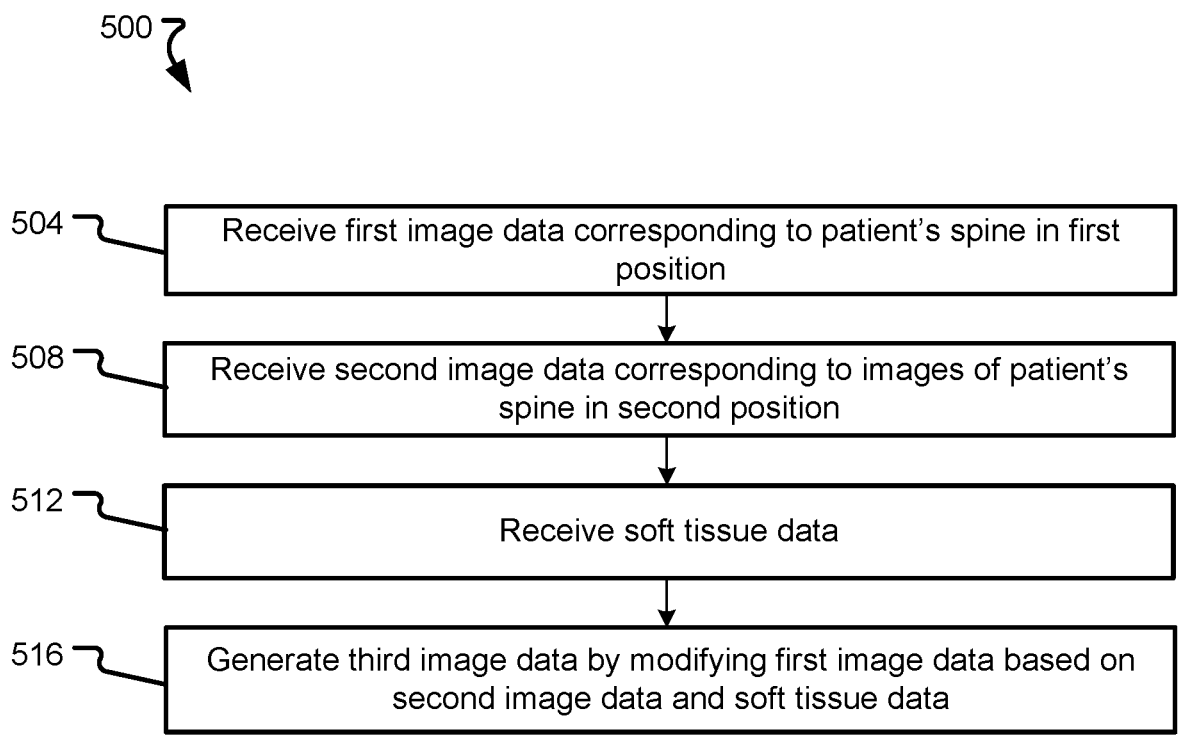
FIG. 5 is a flowchart of a method according to at least one embodiment of the present disclosure.

Turning now to FIG. 5, embodiments of the present disclosure may be used, for example, to generate a virtual image based on (and having the same format as) an actual image of a patient's anatomy or portion thereof, but showing the patient's anatomy or portion thereof in a different position than the actual image. For example, the present disclosure enables generation of a virtual image showing a portion of a patient in a standing position, based on (among other things) an actual image of the same format showing the portion of the patient in a supine position. As another example, the present disclosure enables generation of a virtual image showing a portion of a patient in a prone position, based on (again, among other things) an actual image of the same format showing the portion of the patient in a supine or a standing position. Embodiments of the present disclosure may be used to generate virtual images showing a portion of a patient in a standing position, a prone position, a lateral position, a position of flexion, and a position of extension. The particular position in which the portion of the patient is shown in the virtual image may be selected based on, for example, whether the image will be used for diagnostic or therapeutic purposes.

FIG. 5 depicts a method 500 of generating a virtual image. The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 126) or part of a navigation system (such as a navigation system 114). A processor other than any processor described herein may also be used to execute the method 500. The at least one processor may perform the method 500 by executing instructions (such as the instructions 124) stored in a memory such as the memory 106. The instructions may correspond to one or more steps of the method 500 described below. The instructions may cause the processor to execute one or more algorithms, such as an image processing algorithm 120. The instructions may cause the processor to modify one or more aspects of a biomechanical model 122 to reflect patient-specific characteristics or parameters.

The method 500 comprises receiving first image data corresponding to a patient's spine in a first position (step 504). The first image data comprises first information about a plurality of bony elements of the patient's spine and a plurality of soft tissue elements of the patient's spine. The first image data may be or correspond to an MRI image, or to an image of the patient's spine generating using an imaging modality other than MRI. The first position may be a supine position, a standing position, a prone position, a lateral position, a position of extension, or a position of flexion. One or more aspects of the step 504 may be the same as or substantially similar to one or more aspects of the step 204 of the method 200 described above, and/or vice versa. For example, the first image data may be received in any manner described above in connection with receipt of the initial MRI image in the step 204.

The method 500 also comprises receiving second image data corresponding to at least two images of the patient's spine in a second position different than the first position (step 508). The second image data comprises second information about the plurality of bony elements of the patient spine. The second image data may have been generated using an X-ray imaging device, an ultrasound imaging device, or any other imaging device suitable for generating image data comprising information about bony elements of a patient's spine. The second position may be any position other than the first position, whether a supine position, a standing position, a prone position, a lateral position, a position of extension, or a position of flexion. The at least two images of the patient's spine are offset from each other by at least thirty degrees, or by at least forty degrees, or by at least fifty degrees, or by at least sixty degrees, or by at least seventy degrees, or by at least eighty degrees, or by ninety degrees. One or more aspects of the step 508 may be the same as or substantially similar to one or more aspects of the step 208 of the method 200 described above, and/or vice versa.

The method 500 also comprises receiving soft tissue data corresponding to the plurality of soft tissue elements of the patient's spine (step 512). The soft tissue data may be the same as or substantially similar to the soft tissue information described elsewhere herein, and may include, for example, a biomechanical model and/or data generated using an ultrasound probe. The soft tissue data may be received in any manner described herein, including from or via a database 130, a cloud or other network 132, a communication interface 108, an ultrasound probe or other imaging device 112, and/or a memory 106.

The method 500 also comprises generating third image data by modifying the first image data based on the second image data and the soft tissue data (step 516). The modifying may comprise registering the first information to the second information, in a manner that is the same as or substantially similar to the manner in which the plurality of bony elements in an initial MRI image are registered to a plurality of images in the step 304 described above. The step 516 may also comprise modifying the first image data based on the soft tissue data received in the step 512. Indeed, the step 516 may include one or more aspects of the step 304 and/or the step 308.

The method 500 enables generation of third image data—which may be, comprise, or correspond to a virtual image, for example—that has the same format as the first image data (e.g., an MRI format or other format) but that depicts anatomical elements therein in a position other than the position of the anatomical elements depicted in the first image data. More specifically, the position of the anatomical elements in the third image data corresponds to the position of the anatomical elements in the second image data, which is generated using an imaging modality different than the imaging modality used to generate the first image data.

The present disclosure encompasses embodiments of the method 500 that comprise more or fewer steps than those described above, and/or one or more steps that are different than the steps described above.

Figure 6:
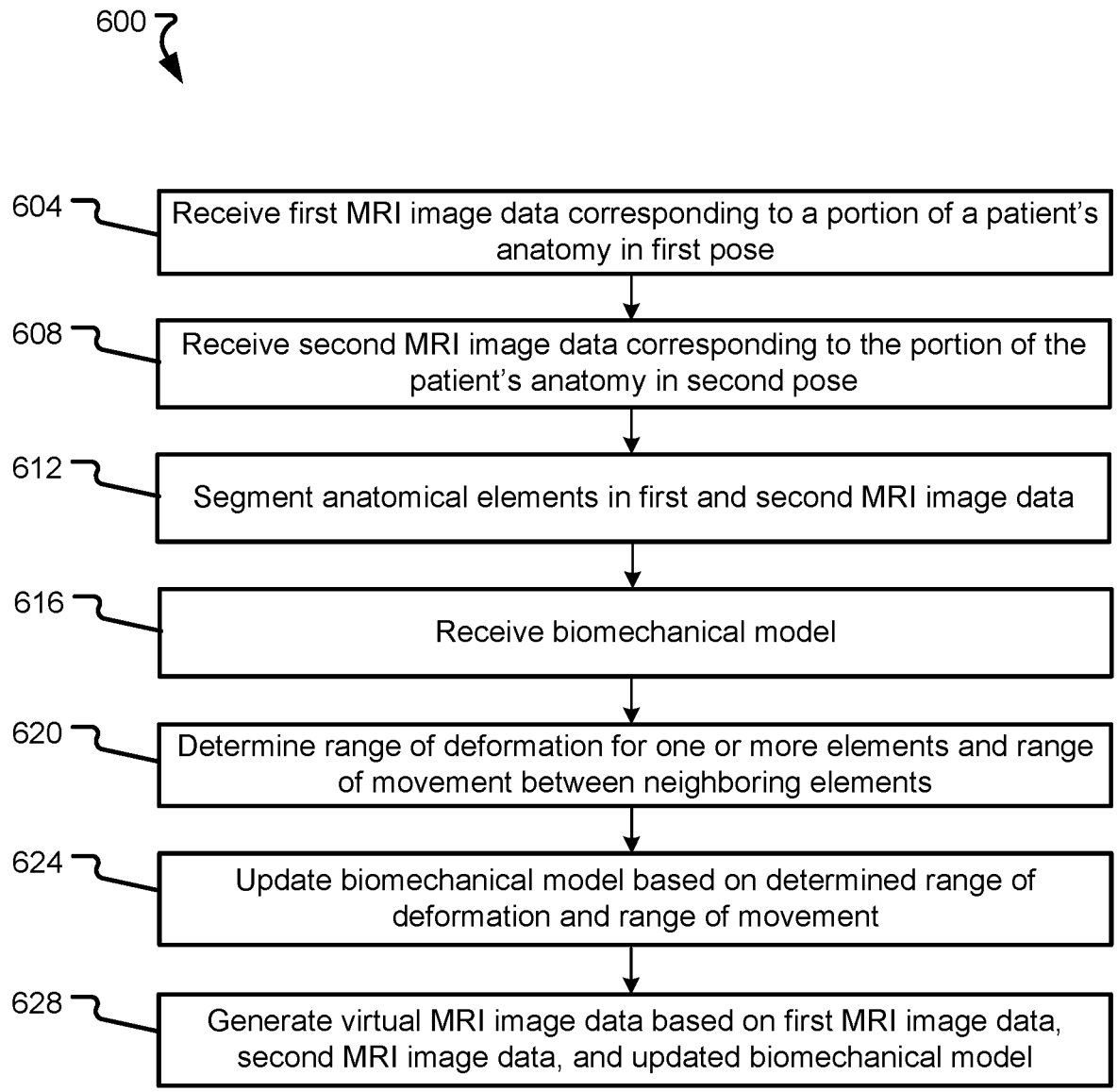
FIG. 6 is a flowchart of a method according to at least one embodiment of the present disclosure.

Turning now to FIG. 6, embodiments of the present disclosure may be used, for example, to generate, based on actual MRI images of a patient in different first and second poses, a virtual MRI image of a patient in a third pose. For example, the first and second poses could be supine and sitting poses, respectively, while the third pose could be a prone pose or a lateral pose.

FIG. 6 depicts a method 600 of generating a virtual MRI image. The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 126) or part of a navigation system (such as a navigation system 114). A processor other than any processor described herein may also be used to execute the method 600. The at least one processor may perform the method 600 by executing instructions (such as the instructions 124) stored in a memory such as the memory 106. The instructions may correspond to one or more steps of the method 600 described below. The instructions may cause the processor to execute one or more algorithms, such as an image processing algorithm 120. The instructions may cause the processor to modify one or more aspects of a biomechanical model 122 to reflect patient-specific characteristics or parameters.

The method 600 comprises receiving first MRI image data corresponding to a portion of a patient's anatomy in a first pose (step 604). The first MRI image data comprises first information about a plurality of bony elements of the patient's anatomy and a plurality of soft tissue elements of the patient's anatomy. Although described as MRI image data, the first image data may be or correspond to an image of the patient's anatomy generated using an imaging modality other than MRI. The first pose may be, for example, a supine pose, a standing pose, a sitting pose, a lateral pose, a prone pose, an extension pose, or a flexion pose. One or more aspects of the step 604 may be the same as or substantially similar to one or more aspects of the step 204 of the method 200 described above, and/or vice versa. For example, the first MRI image data may be received in any manner described above in connection with receipt of the initial MRI image in the step 204.

The method 600 also comprises receiving second MRI image data corresponding to the portion of the patient's anatomy in a second pose (step 608). The second MRI image data comprises second information about the plurality of bony elements of the patient's anatomy and the plurality of soft tissue elements of the patient's anatomy. Here again, although described as MRI image data, the second image data may be or correspond to an image of the patient's anatomy generated using an imaging modality other than MRI. The second pose may be any pose other than the first pose, and may in some embodiments be a pose that differs from the first pose in that some or all of the plurality of bony elements and/or soft tissue elements in the portion of the patient's anatomy are themselves in a different pose relative to each other. The second pose may be, for example, a supine pose, a standing pose, a sitting pose, a lateral pose, a prone pose, an extension pose, or a flexion pose. As with the step 604, one or more aspects of the step 608 may be the same as or substantially similar to one or more aspects of the step 204 of the method 200 described above, and/or vice versa. For example, the first MRI image data may be received in any manner described above in connection with receipt of the initial MRI image in the step 204.

The method 600 also comprises segmenting anatomical elements in each of the first MRI image data and the second MRI image data (step 612). The step 612 comprises the same or substantially similar actions as set forth with respect to the step 216 of the method 200 described above. All of the anatomical elements depicted in each of the first MRI image data and the second MRI image data may be segmented, or only a subset of anatomical elements depicted in each set of data may be segmented. For example, in some embodiments, only bony anatomical elements or only soft tissue anatomical elements may be segmented, while in other embodiments both bony and soft tissue anatomical elements may be segmented. Alternatively, only anatomical elements in a particular portion of each data set may be segmented. For example, only anatomical elements of a portion of the patient's anatomy that appears in both the first MRI image data and the second MRI image data may be segmented.

Additionally, the step 612 comprises matching corresponding anatomical elements in the first MRI image data and the second MRI image data. In other words, if each of the first MRI image data and the second MRI image data depict a particular vertebra, then the step 612 comprises establishing a correlation between the depiction of that vertebra in the first image data and in the second image data. The matching may occur for every segmented anatomical element that appears in both the first image data and in the second image data, or for only a subset of the segmented anatomical elements. In some embodiments, the matching may be attempted for every segmented anatomical element that appears in the first MRI image data or in the second MRI image data, and discontinued for those segmented anatomical elements that are determined not to be depicted in both the first MRI image data and the second MRI image data.

The method 600 also comprises receiving a biomechanical model of the portion of the patient's anatomy depicted in the first MRI image data and the second MRI image data (step 616). The biomechanical model may be a biomechanical model 122, and/or may be the same as or similar to any other biomechanical model described herein. For example, the biomechanical model may be a parametric biomechanical model. The biomechanical model may be received in any manner described herein, including from a memory 106, a database 130, a cloud 132, and/or via a communication interface 108.

The method 600 also comprises determining a range of deformation of one or more anatomical elements and a range of movement between neighboring anatomical elements (step 620). The determining a range of deformation may comprise comparing a pose of each of the one or more anatomical elements in the first MRI image data to a pose of each of the one or more anatomical elements in the second MRI image data, and measuring a difference in pose (whether in terms of one or more angles, one or more distances, or otherwise). Where, for example, the first MRI image and the second MRI image do not show a given anatomical element at opposite ends of the given anatomical element's range of deformation, the determining may further comprise extrapolation to predict the full range of deformation of the given anatomical element.

The determining a range of movement between neighboring elements may comprise, for example, identifying adjacent pairs of anatomical elements in the first MRI image data and corresponding pairs of anatomical elements in the second MRI image data, and comparing how the anatomical elements in each pair are positioned/oriented relative to each other in each image. The comparing may comprise measuring a difference in relative pose of the pair of anatomical elements (whether in terms of one or more angles, one or more distances, or otherwise). Here again, where the first MRI image and the second MRI image do not show a given pair of anatomical elements at opposite ends of the pair's range of movement, the determining the range of movement may further comprise extrapolation to predict the full range of deformation of the given pair of anatomical elements.

The method 600 also comprises updating the biomechanical model based on the determined range of deformation and range of movement. The updating may comprise inputting the determine range of deformation and range of movement into a generic parametric biomechanical model to render the biomechanical model patient-specific. In some embodiments, the updating may further comprise inputting one or more measurements of one or more anatomical elements into the biomechanical model, so that the biomechanical model accurately reflects the patient's anatomy in terms of size and pose of the patient's anatomical elements, as well as in terms of range of deformation and range of movement of the patient's anatomical elements. The result of the updating is a biomechanical model that reflects at least the determined range of deformation and the determined range of movement, and possibly also one or more other patient-specific aspects of the anatomical elements included within the biomechanical model.

The method 600 also comprises generating third MRI image data based on the first MRI image data, the second MRI image data, and the updated biomechanical model (step 516). The third MRI image data is virtual MRI image data showing the portion of the patient's anatomy in a third pose different that the first pose and the second pose. The third pose may be, for example, a supine pose, a standing pose, a sitting pose, a lateral pose, a prone pose, an extension pose, or a flexion pose.

The generating may comprise, for example, manipulating the biomechanical model to reflect the third pose, and then re-arranging one or more of the segmented anatomical elements from the first MRI image data and/or the second MRI image data to match the pose of the corresponding anatomical element as shown in the biomechanical model. The accuracy of the third MRI image data may depend, for example, on the accuracy of the updated biomechanical model, and more specifically on how accurately the biomechanical model reflects the actual range of deformation of the one or more anatomical elements and the actual range of movement between the neighboring anatomical elements in the portion of the patient's anatomy.

The present disclosure encompasses embodiments of the method 600 that comprise more or fewer steps than those described above, and/or one or more steps that are different than the steps described above.

As discussed above, embodiments of the present disclosure beneficially enable surgeons and other medical professionals to benefit from improved diagnostic and therapeutic information while reducing costs to the patient by reducing the usage of expensive imaging modalities, such as magnetic resonance imaging. Embodiments of the present disclosure also beneficially enable the generation of detailed image data reflecting one or more particular positions of a patient even when the patient cannot be directly imaged in that position using an imaging modality that would provide the desired level of detail, whether due to unavailability of capable imaging devices, the physical constraints associated with the use of such imaging devices, and/or physical constraints of the patient. This is particularly the case when a patient is positioned on an operating table in advance of or during an operation and needs to be imaged in that position, at which time imaging of the patient using an MRI machine is at least impractical and at most impossible. However, using embodiments of the present disclosure, a virtual MRI image may be generated based on an MRI image and one or more X-ray or other types of images that show at least the bony elements of the patient. Additionally, using embodiments of the present disclosure, a virtual MRI image may be generated based on an MRI image and one or more ultrasound or other images that show at least the soft tissue elements of the patient. And, using embodiments of the present disclosure, a virtual MRI image of a patient in a third pose may be generated based on an MRI image of the patient in a first pose and an MRI image of a patient in a second pose different than the first pose.

As may be appreciated based on the foregoing disclosure, the present disclosure encompasses methods with fewer than all of the steps identified in FIGS. 2, 3, 4, 5, and 6 (and the corresponding description of the methods 200, 300, 400, 500, and 600), as well as methods that include additional steps beyond those identified in FIGS. 2, 3, 4, 5 and 6 (and the corresponding description of the methods 200, 300, 400, 500, and 600). One or more steps of the methods described herein may be performed in an order other than the order in which they are described herein.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of generating a virtual magnetic resonance imaging (MRI) image, the method comprising:
   receiving, from an MRI imaging device, an initial preoperative MRI image of a patient in a supine position, the initial preoperative MRI image depicting at least a portion of an anatomy of the patient;
   receiving, from an imaging device different from the MRI imaging device, a plurality of intraoperative images of the patient in a prone position, each of the plurality of intraoperative images depicting at least a plurality of bony elements within the portion of the patient's anatomy;
   segmenting the initial preoperative MRI image to identify a depiction of each of the plurality of bony elements and each of a plurality of soft tissue elements within the initial preoperative MRI image, wherein the segmenting enables each of the plurality of soft tissue elements to be modified relative to one another within the initial preoperative MRI image;
   determining a range of deformation and a range of movement of one or more elements of the plurality of bony elements;
   generating the virtual MRI image based on the initial preoperative MRI image, the plurality of intraoperative images of the patient in the prone position, and a biomechanical model corresponding to at least the plurality of soft tissue elements associated with the patient, wherein generating the virtual MRI image comprises modifying a first soft tissue element of the plurality of soft tissue elements using the biomechanical model without modifying a second soft tissue element of the plurality of soft tissue elements; and
   guiding, using the virtual MRI image, a robotic arm relative to the anatomy of the patient.

2. The method of claim 1, wherein generating the virtual MRI image comprises:
   registering each of the plurality of bony elements in the initial preoperative MRI image to a corresponding one of the plurality of bony elements depicted in each of the plurality of intraoperative images.

3. The method of claim 1, wherein generating the virtual MRI image further comprises:
   updating, based on the range of deformation and the range of movement, the biomechanical model.

4. The method of claim 1, wherein the biomechanical model comprises ultrasound information corresponding to at least some of the portion of the patient's anatomy.

5. The method of claim 1, wherein the plurality of intraoperative images provides orthogonal views of the portion of the patient's anatomy.

6. The method of claim 1, wherein the virtual MRI image is generated without the patient being imaged by the MRI imaging device when in the prone position.

7. The method of claim 1, wherein the plurality of intraoperative images comprises at least one X-ray image.

8. The method of claim 1, wherein the plurality of intraoperative images comprises at least one ultrasound image.

9. A system for generating a virtual magnetic resonance imaging (MRI) image, the system comprising:
   an imaging device capable of imaging hard tissue;
   a processor; and
   a memory storing instructions for execution by the processor that, when executed, cause the processor to:
   receive, from an MRI imaging device, a first MRI image of a patient in a supine position, the first MRI image depicting hard tissue and soft tissue of the patient;
   receive a plurality of images of the patient in a prone position different than the supine position, the plurality of images generated by the imaging device that is different from the MRI imaging device, wherein the patient is in the supine position preoperatively, and wherein the patient is in the prone position intraoperatively;
   receive soft tissue information corresponding to the patient;
   process the first MRI image to identify a plurality of bony elements and a plurality of soft tissue elements therein, wherein the processing enables each of the plurality of soft tissue elements to be modified relative to one another within the first MRI image;
   determine a range of deformation and a range of movement of one or more bony elements of the plurality of bony elements;
   generate a virtual second MRI image by registering each of the plurality of bony elements in the first MRI image to a corresponding bony element in the plurality of images, and by updating the plurality of soft tissue elements in the first MRI image based on the soft tissue information corresponding to the patient, wherein updating the plurality of soft tissue elements comprises modifying a first soft tissue element of the plurality of soft tissue elements using the soft tissue information without modifying a second soft tissue element of the plurality of soft tissue elements; and
   guide, using the virtual second MRI image, a robotic arm relative to the patient.

10. The system of claim 9, further comprising:
an ultrasound probe; and
a second robotic arm configured to manipulate at least one of the imaging device and the ultrasound probe.

11. The system of claim 10, wherein the instructions stored in the memory, when executed, further cause the processor to:
cause the second robotic arm to move the ultrasound probe to a plurality of positions to generate the soft tissue information.

12. The system of claim 9, wherein each of the plurality of bony elements is a vertebra.

13. The system of claim 9, wherein the plurality of soft tissue elements comprises at least one of a ligament and an intervertebral disc.

14. The system of claim 9, wherein the soft tissue information comprises a biomechanical model.

15. A method of modifying image data, the method comprising:
receiving first image data corresponding to a patient's spine in a supine position, the first image data comprising first information about a plurality of bony elements of the patient's spine and a plurality of soft tissue elements of the patient's spine, wherein the first image data is generated preoperatively;
receiving second image data corresponding to at least two images of the patient's spine in a prone position different than the supine position, the second image data comprising second information about the plurality of bony elements of the patient's spine, wherein the second image data is generated intraoperatively;
receiving soft tissue data corresponding to the plurality of soft tissue elements of the patient's spine;
determining a range of deformation and a range of movement of one or more bony elements of the plurality of bony elements;
generating third image data by modifying the first image data based on the second image data and the soft tissue data, the modifying comprising registering the first information to the second information and further comprising changing a first soft tissue element of the plurality of soft tissue elements using the soft tissue data without changing a second soft tissue element of the plurality of soft tissue elements; and
guiding, using the third image data, a robotic arm relative to the patient's spine.

16. The method of claim 15, wherein the first image data is generated using magnetic resonance imaging, and wherein the second image data is generated without using the magnetic resonance imaging.

17. The method of claim 15, wherein the at least two images are offset by at least thirty degrees.

18. The method of claim 15, wherein the at least two images are orthogonal.

19. The method of claim 15, wherein the first image data is in a first format, the second image data is in a second format different than the first format, and the third image data corresponds to a virtual image in the first format of the patient's spine in the prone position.

* * * * *